US007223739B1

(12) United States Patent
Haynes et al.

(10) Patent No.: US 7,223,739 B1
(45) Date of Patent: May 29, 2007

(54) ADJUVANTED GENETIC VACCINES

(75) Inventors: Joel R. Haynes, Madison, WI (US);
Georg Widera, Del Mar, CA (US);
James T. Fuller, Madison, WI (US);
Timothy Shipley, Madison, WI (US);
Deborah Fuller, Madison, WI (US);
Mary Wu, Madison, WI (US)

(73) Assignee: Powderject Vaccines, Inc., Wilmington, DE (US)

( * ) Notice: Subject to any disclaimer, the term of this patent is extended or adjusted under 35 U.S.C. 154(b) by 0 days.

(21) Appl. No.: 09/433,777

(22) Filed: Nov. 3, 1999

Related U.S. Application Data

(63) Continuation-in-part of application No. 09/122,931, filed on Jul. 27, 1998, now abandoned, which is a continuation of application No. 08/472,085, filed on Jun. 7, 1995, now abandoned.

(51) Int. Cl.
*A61K 48/00* (2006.01)
*A61K 47/02* (2006.01)
*A61K 45/00* (2006.01)
*C12N 15/63* (2006.01)

(52) U.S. Cl. .................. 514/44; 424/278.1; 424/283.1; 424/490; 435/320.1; 435/455

(58) Field of Classification Search ................ 514/44; 435/325, 320.1; 424/93.2, 277.1, 184.1
See application file for complete search history.

(56) References Cited

U.S. PATENT DOCUMENTS

| 4,945,050 A | 7/1990 | Sanford et al. |
| 5,015,580 A | 5/1991 | Christou et al. |
| 5,036,006 A | 7/1991 | Sanford et al. |
| 5,100,792 A | 3/1992 | Sanford et al. |
| 5,112,749 A | 5/1992 | Brey, III et al. |
| 5,120,657 A | 6/1992 | McCabe et al. |
| 5,149,655 A | 9/1992 | McCabe et al. |
| 5,204,253 A | 4/1993 | Sanford et al. |
| 5,584,807 A | 12/1996 | McCabe |
| 5,589,466 A | 12/1996 | Felgner et al. |
| 5,630,796 A | 5/1997 | Bellhouse et al. |
| 5,738,852 A | 4/1998 | Robinson et al. |
| 5,865,796 A | 2/1999 | McCabe |
| 5,925,362 A * | 7/1999 | Spitler et al. ............ 424/277.1 |
| 6,168,587 B1 | 1/2001 | Bellhouse et al. |
| 6,194,389 B1 | 2/2001 | Johnston et al. |

FOREIGN PATENT DOCUMENTS

| WO | WO 91/00359 A1 | 1/1991 |
| WO | WO 91/07487 A1 | 5/1991 |
| WO | WO 93/17706 A1 | 9/1993 |
| WO | WO 94/24263 | 10/1994 |
| WO | WO 95/19799 | 7/1995 |
| WO | WO 96/04947 | 2/1996 |
| WO | WO 96/12513 | 5/1996 |
| WO | WO 96/14855 | 5/1996 |
| WO | WO 96/20022 | 7/1996 |
| WO | WO 97/40163 A1 | 1/1997 |
| WO | WO 97/32987 | 9/1997 |
| WO | WO 97/48485 | 12/1997 |
| WO | WO 98/10750 | 3/1998 |
| WO | WO 98/46263 | 10/1998 |
| WO | WO 99/27961 | 6/1999 |
| WO | WO 00/12121 | 3/2000 |
| WO | WO 00/13704 | 3/2000 |

OTHER PUBLICATIONS

Sedegah et.al.; Protection aganist malaria by immunization with plasmid DNA encoding circumsporozoite protein, 1994, Proc. Natl. Acad., vol. 91: 9866-9870.*
Abbas et.al.; Functional diversity of helper T Lymphocytes, 1996, Nature, vol. 383: 787-783.*
Golding et.al.; The Potential for Recruiting Immune Responses Toward Type 1 or Type 2 T Cell Help, 1994, American Society if Tripical Medicine and Hygiene: 33-40.*
Haynes J R, "Generic Vaccines," *Infectious Disease Clinincs Of North America*. 13(1):11-26 (1999).
Sasaki et al., "The Search for a Potent DNA Vaccine against AIDS: The Enhancement of Immunogenicity by Chemical & Genetic Adjuvants", *Anticancer research* 18:3907-3916 (1998).
Sasaki et al., "Monophosphoryl Lipid A Enchances Both Humoral & Cell-Mediated Immune Responses to DNA Vaccination against Human Immunodeficiency Virus Type 1", *Infection & immunity*. 65(9):3520-3528 (1997).
Lodmell et al., "DNA Vaccination of mice against rabies virus: effects of the route of vaccination and adjuvent monophosphoryl lipid A (MPL)" *Vaccine*. 18:1059-1066 (2000).
Pow & Crook, "Extremely high titre polyclonal antisera against small neurotransmitter molecules: rapid production, Charcterisation and use in light-and electron-microscopic immunocytochemistry", *J. of Neuroscience Methods*. 48:51-63 (1993).
Larsen et al., "Coadministration of DNA Encoding Interleukin-6 and Hemagglutinin Confers Protection from Influenza Virus Challenge in Mice", Journal of Virology, Feb. 1997, pp. 1704-1708, vol. 72, No. 2.
ICN Biochemicals, Inc., "Biochemicals, Organic Chemicals, Radiochemicals, Cell Biology, Immuno Biologicals, Diagnostics", Index, ICN Biochemicals, Inc. 3300 Hyland Avenue, Costa Mesa, CA (1991-1992).
Johnston et al., "Biolistic Transformation of Animal Tissue", In Vitro Cell. Dev. Biol. 27, Jan. 1991, pp. 11-14.
Klein et al., "High-Velocity Microprojectiles for Delivering Nucleic Acids into Living Cells", Nature, pp. 70-73, vol. 327, May 7, 1987.
Orkin et al., "Report and Recommendations of the Panel to Assess the NIH Investment in Research on Gene Therapy", Dec. 7, 1995.
Sanford et al., "Delivery of Substrates into Cells and Tissues Using a Particle Bombardment Process", Particulate Science and Technology 5, 1987, pp. 27-37, Hemisphere Publishing Corporation.
Clinical Research, Apr. 1994, vol. 42, No. 2.

(Continued)

*Primary Examiner*—Anne Marie Wehbé
(74) *Attorney, Agent, or Firm*—Foley & Lardner LLP

(57) ABSTRACT

Reagents useful in nucleic acid immunization techniques are described. More particularly, adjuvanted genetic vaccine compositions are described, as are methods of using those compositions for inducing an enhanced immune response against a selected antigen.

29 Claims, 1 Drawing Sheet

OTHER PUBLICATIONS

Stryer, "Synthesis of a Specific Antibody Following Exposure to an Antigen", 1975, p. 732, W.H. Freeman and Company, San Francisco, CA.

Tang et al., "Genetic Immunization is a Simple Method for Eliciting an Immune Response", Nature, Mar. 12, 1992, pp. 152-154, vol. 356.

Ulmer et al., "Heterologous Protection Against Influenza by Injection of DNA Encoding a Viral Protein", Science, Mar. 19, 1993, pp. 1745-1749, vol. 259.

Yang et al., "In Vivo and In Vitro Gene Transfer to Mammalian Somatic Cells by Particle Bombardment," Proc. Natl. Acad. Sci. USA, Dec. 1990, pp. 9568-9572, vol. 87.

Xiang et al., "Manipulation of the Immune Response to a Plasmid-Encoded Viral Antigen by Coinoculation with Plasmids Expressing Cytokines", Immunity, Feb. 1995, pp. 129-135, vol. 2, Cell Press.

* cited by examiner

SEQUENCE LISTING

<160> NUMBER OF SEQ ID NOS: 7

<210> SEQ ID NO 1
<211> LENGTH: 10
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 1
gccaccatgg                                                                10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gcccccatgg                                                                10

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tccatgacgt tcctgatgct                                                     20

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gactctcgag cgttctc                                                        17

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Tyr Gln Arg Thr Arg Ala Leu Val
  1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Gly Pro Gly Arg Ala Phe Val Thr Ile
  1               5                  10
```

```
<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ile Pro Gln Ser Leu Asp Ser Trp Trp Thr Ser Leu
 1               5                  10
```

ADJUVANTED GENETIC VACCINES

CROSS REFERENCE TO RELATED APPLICATIONS

This application is a continuation-in-part of U.S. patent application Ser. No. 09/122,931, filed 27 Jul. 1998, now abandoned which is a Rule 1.53(b)(1) continuation of U.S. patent application Ser. No. 08/472,085, filed 7 Jun. 1995, now abandoned, from which applications priority is claimed pursuant to 35 U.S.C. §120 and which applications are incorporated herein by reference in their entireties.

TECHNICAL FIELD

The invention relates to the general fields of molecular biology and immunology, and generally relates to reagents useful in nucleic acid immunization techniques. More particularly the invention relates to vaccine compositions and methods of using those compositions for inducing an enhanced immune response against a selected antigen.

BACKGROUND TO THE INVENTION

Techniques for the injection of DNA and mRNA into mammalian tissue for the purposes of immunization against an expression product have been previously described. See, e.g., European Patent Specification EP 0 500 799 and U.S. Pat. No. 5,589,466. The techniques, termed "nucleic acid immunization" herein, have been shown to elicit both humoral and cell-mediated immune responses. For example, sera from mice immunized with a DNA construct encoding the envelope glycoprotein, gp160, were shown to react with recombinant gp160 in immunoassays, and lymphocytes from the injected mice were shown to proliferate in response to recombinant gp120. Wang et al. (1993) *Proc. Natl. Acad. Sci. USA* 90:4156–4160. Similarly, mice immunized with a human growth hormone (hGH) gene demonstrated an antibody-based immune response. Tang et al. (1992) *Nature* 356:152–154. Intramuscular injection of DNA encoding influenza nucleoprotein driven by a mammalian promoter has been shown to elicit a CD8+ cytolytic T lymphocyte (CTL) response that can protect mice against subsequent lethal challenge with virus. Ulmer et al. (1993) *Science* 259:1745–1749. Immunohistochemical studies of the injection site revealed that the DNA was taken up by myeloblasts, and cytoplasmic production of viral protein could be demonstrated for at least 6 months.

These so-called "genetic vaccines" have thus been demonstrated to elicit immune response in treated animals similar to those observed following administration of live attenuated vaccines, the most effective form of vaccine in use today. The theoretical effectiveness of nucleic acid-based vaccines stems from the ability of the vaccine compositions to elicit the de novo production of correctly folded protein antigens, which can result in the elicitation of antibody responses recognizing complex three dimensional epitopes. In addition, the in vivo production of these antigens in professional antigen presenting cells results in the presentation of processed peptide fragments by MHC class I molecules, resulting in the activation and participation of antigen-specific cytolytic T lymphocytes (CTLs).

To date, the most effective nucleic acid immunization technique involves delivery of a DNA vaccine composition via particle-mediated, intracellular delivery into the epidermis. See, e.g., European Patent No. 0 500 799. This technique avoids the pitfalls of extracellular delivery (e.g., via needle and syringe delivery to skin or muscle) since it is believed that most of such extracellularly delivered DNA is rapidly degraded, necessitating that an excess amount of DNA be inoculated just to achieve a sufficient level of antigen expression. Particle-mediated DNA delivery to the epidermis, on the other hand, achieves the direct, intracellular deposition of plasmid DNAs into epidermal cells, including epidermal Langerhans cells. Because of the direct intracellular delivery, the DNA is protected from extracellular nucleases and only very small quantities of DNA need be delivered. In fact, particle-mediated immunization with nanogram quantities of a given plasmid DNA can result in the elicitation of very strong humoral and CTL responses, often following a single administration.

Malaria is a widespread and significant human disease, particularly in tropical countries. Disease is caused by the mosquito borne parasites *Plasmodium falciparum* and *Plasmodium vivax*. Yet malaria vaccine research has yet to result in the development of a safe, practical, and effective prophylactic vaccine product. Although numerous examples of significant immune response have been elicited in both animal models and human volunteers using a variety of experimental vaccines, the actual protection afforded by such vaccinations in human clinical trials has been disappointingly low. The increased scientific understanding of the life cycle of the malaria parasite and the identification of important antigens from various parasite life stages have allowed the development of a variety of vaccine strategies designed to elicit the formation of protective antibodies as well as cellular effector cells such as CTLs.

The disease cycle of malaria begins with a mosquito bite that injects the infectious malaria sporozoites into the bloodstream. It would thus seem reasonable that sporozoite-specific antibodies would be an effective means of preventing or significantly limiting the infection of hepatocytes at this stage. Following hepatocyte infection, however, the parasite develops intracellularly in the hepatocyte and may escape circulating antibodies. At this stage, the presentation of sporozoite-specific antigens on the surface of the infected hepatocytes prior to merozoite or blood stage merozoite release provides an attractive target for malaria-specific CTLs. Such effector cells could either eliminate the infected hepatocytes or elicit the destruction of intracellular parasites, prior to first release of mature blood stage merozoites.

SUMMARY OF THE INVENTION

It is a primary object of the present invention to provide novel compositions for use in nucleic acid (genetic) vaccination procedures. These compositions combine nucleic acid molecules that contain sequences encoding an antigen of interest with an adjuvant, where the adjuvant is present in the composition in a form other than DNA, and are intended for direct, intracellular delivery of the composition—both the sequence encoding the antigen and the non-DNA adjuvant. Accordingly, the present compositions represent a significant departure from previous DNA vaccine compositions that may combine antigen-encoding sequences with adjuvant-encoding sequences. In addition, the purposeful delivery of the non-DNA adjuvant into a target cell is counter-intuitive since adjuvants are known to operate on an extracellular basis, for example by forming an extracellular depot, and it is when these moieties are present in the extracellular realm that immune-competent cells can encounter and interact with the adjuvant to bring about a desired adjuvant effect. The adjuvant component of these novel compositions can be provided in a number of different forms such as, but not limited to, in the form of a protein, a lipid, a non-protein hormone or analog thereof, a vitamin or an analog thereof, a purified protein derivative from a bacterial culture (e.g., *Bacillus calmette* guerin), a mycobacterial cell wall skeletal material, a saponin or derivative thereof, or the like.

Accordingly, the invention provides a composition that contains (a) a nucleic acid molecule comprising a sequence encoding an antigen of interest; and (b) an adjuvant that is effective to enhance at least one component of an immune response directed against the antigen when it is expressed in the cells of a vaccinated individual, wherein the adjuvant is present in the composition in a form that is other than a DNA. In particular embodiments, the nucleic acid molecule in provided in the context of a vector construct, preferably a plasmid. The composition is also preferably coated onto a core carrier particle, for example onto a gold or tungsten ballistic carrier particle. The selected antigen can be obtained or derived from any agent that one wishes to elicit an immune response against, and can thus be from an infectious or parasitic disease agent, a tumor-specific or a "self" antigen, an allergen, or the like. In particular embodiments, the antigen is a viral antigen, such as an antigen from a hepatitis B virus (HBV), a human immunodeficiency virus (HIV) or an influenza virus. In other embodiments, the antigen is from a parasite, such as from a malarial parasite. The selected adjuvant can be any suitable adjuvant composition. In particular embodiments, the adjuvant is at least partially soluble in ethanol. Preferred adjuvants include monophosphoryl lipid A (MPL), and saponins such as Quil-A. Other preferred adjuvants are the so-called immune shift adjuvants as described herein. All of these compositions can be used in the manufacture of a medicament for use in nucleic acid immunization techniques.

The invention also provides methods of using the above-described compositions to elicit an immune response against a selected antigen in a vaccinated individual. The methods entail delivering the compositions directly into cells present at a target site in the individual in an amount sufficient to bring about the desired immune response. In particular embodiments, the composition is first coated onto a core carrier particle (e.g., a gold or tungsten ballistic particle) and administered using a transdermal delivery technique, such as a particle-mediated delivery technique. A preferred target tissue is thus epidermal tissue.

It is also a primary object of the present invention to provide novel compositions for use in nucleic acid (genetic) vaccination procedures which compositions are formed from the combination of a nucleic acid molecule that contains a sequence encoding an antigen of interest and an immune shift adjuvant which is effective to enhance the Th1 component of an immune response elicited against the antigen in a vaccinated individual. Here again the immune shift adjuvant is present in the composition in a form other than DNA, and the composition is intended for direct, intracellular delivery. In particular embodiments, the antigen is from an infectious or parasitic disease agent and/or the immune shift adjuvant is monophosphoryl lipid A. The composition can be coated onto a core carrier particle to provide a pharmaceutical preparation.

It is yet a further object of the present invention to provide a method for eliciting an immune response against a selected antigen in an individual (e.g., vaccinating against an infectious disease agent) which includes the steps of delivering into the cells of the individual a genetic construct which causes expression in the cells of the individual of an antigen at sufficient levels to bring about an antigen-specific immune response; and coadministering to the individual in the vicinity of the delivery of the genetic construct an effective amount of an immune shift adjuvant sufficient to cause a shift in the balance of Th1 and Th2 type immune responses elicited in the vaccinated individual from that response which would be obtained without the immune shift adjuvant. The present invention thus facilitate the use of genetic vaccines through the use of immune shift adjuvants which alter or re-direct the immunological response of a individual to a genetic vaccine.

Accordingly, the invention provides a method of generating an immune response, comprising: (a) delivering a genetic vaccine composition into cells present at a target site in a subject, wherein the vaccine composition comprises a nucleic acid encoding an antigen; and (b) coadministering an adjuvant, wherein the adjuvant composition may be administered to the same or different site as the vaccine composition. The adjuvant composition may also be delivered prior to, subsequent to, or concurrently with the vaccine composition. The adjuvant and vaccine compositions may be administered in either a single composition or as separate compositions. In one particular embodiment, the adjuvant composition is in particulate form and delivered using a transdermal delivery technique, preferably using a needless syringe powder injection device. In a related embodiment, the adjuvant is administered using a particle-mediated delivery technique. For both of these embodiments, the preferred target site is epidermal tissue. In yet another embodiment, the adjuvant is administered topically to the target site.

It is a still further object of the invention to provide an efficacious genetic vaccine composition for malaria. The composition includes a genetic construct encoding the expression in an individual of one or more malarial antigens, e.g., a CS antigen; and an effective quantity of an immune shift adjuvant sufficient to shift the nature of the immune response elicited in a vaccinated individual from a predominantly Th2 response toward a Th1 response.

It is an advantage of the present invention that the efficacy of genetic vaccine compositions can be enhanced. It is another advantage that the methods and compositions described herein can be used to specifically tailor or alter the nature of an immune response engendered using a genetic vaccine compositions.

These and other objects, embodiments and advantages of the invention will readily occur to those of ordinary skill in the art in view of the disclosure herein.

DETAILED DESCRIPTION OF THE PREFERRED EMBODIMENTS

Figure 1:
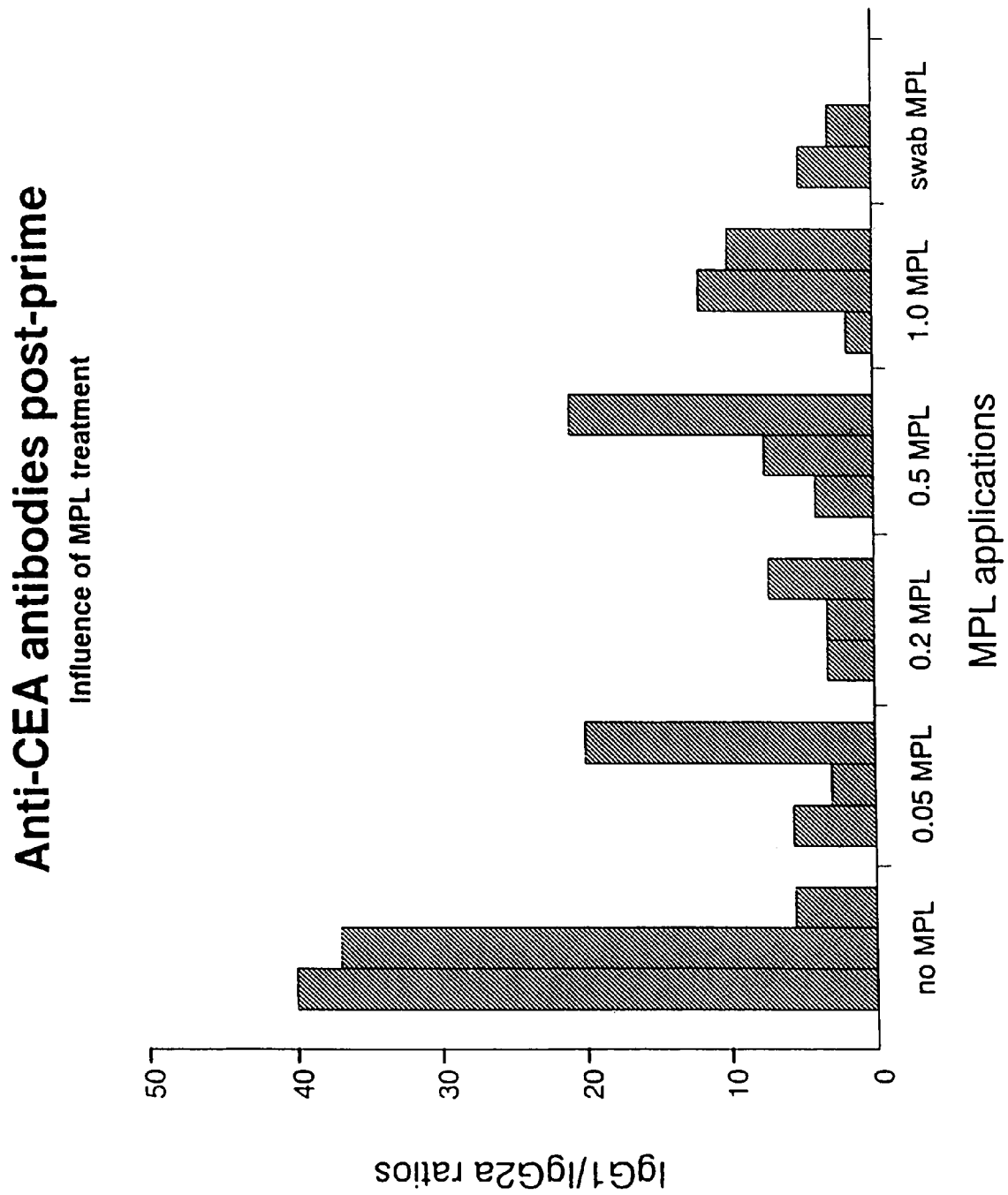
FIG. 1 is a histogram representing the results of Experiment 1.

Before describing the present invention in detail, it is to be understood that this invention is not limited to particular vaccine formulations or process parameters as such may, of course, vary. It is also to be understood that the terminology used herein is for the purpose of describing particular embodiments of the invention only, and is not intended to be limiting.

It must be noted that, as used in this specification and the appended claims, the singular forms "a," "an" and "the" include plural referents unless the content clearly dictates otherwise. Thus, for example, reference to "a particle" includes two or more particles, reference to "an antigen" or "an adjuvant" includes a mixture or a combination of two or more such agents, reference to "an excipient" includes mixtures or combinations of two or more excipients, and the like.

A. Definitions

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed, and are intended to be defined as indicated below.

As used herein, the term "transdermal delivery" includes intradermal (e.g., into the dermis or epidermis) and transdermal (e.g. "percutaneous") i.e., delivery by passage of an agent into or through at least a top layer of skin. See, e.g., *Transdermal Drug Delivery: Developmental Issues and Research Initiatives*, Hadgraft and Guy (eds.), Marcel Dekker, Inc., (1989); *Controlled Drug Delivery*: Fundamentals and Applications, Robinson and Lee (eds.), Marcel Dekker Inc., (1987); and *Transdermal Delivery of Drugs*, Vols. 1–3, Kydonieus and Berner (eds.), CRC Press, (1987).

An "antigen" refers to any immunogeneic moiety or agent, generally a macromolecule, which can elicit an immunological response in an individual. The term may be used to refer to an individual macromolecule or to a homogeneous or heterogeneous population of antigenic macromolecules. As used herein, the term "antigen" includes allergens. Thus, the term "antigen" broadly encompasses moieties including proteins, polypeptides, antigenic protein fragments, oligosaccharides, polysaccharides, organic or inorganic chemicals or compositions, and the like. Furthermore, the antigen can be derived or obtained from any virus, bacterium, parasite, protozoan, or fungus, and can be a whole organism. The term also includes tumor antigens or so-called "self" antigens that are involved with autoimmune disease. Similarly, an oligonucleotide or polynucleotide which expresses an antigen, such as in nucleic acid immunization applications, is also included in the definition. Synthetic antigens are also included, for example, polyepitopes, flanking epitopes, and other recombinant or synthetically derived antigens (Bergmann et al. (1993) *Eur. J. Immunol.* 23:2777–2781; Bergmann et al. (1996) *J. Immunol.* 157:3242–3249; Suhrbier, A. (1997) *Immunol. and Cell Biol.* 75:402–408; Gardner et al. (1998) 12th World AIDS Conference, Geneva, Switzerland, Jun. 28–Jul. 3, 1998).

The terms "nucleic acid molecule" and "polynucleotide" are used interchangeably and refer to a polymeric form of nucleotides of any length, either deoxyribonucleotides or ribonucleotides, or analogs thereof. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A "gene" as used in the context of the present invention is a sequence of nucleotides in a nucleic acid molecule (chromosome, plasmid, etc.) with which a genetic function is associated. A gene is a hereditary unit, for example of an organism, comprising a polynucleotide sequence (e.g., a DNA sequence for mammals) that occupies a specific physical location (a "gene locus" or "genetic locus") within the genome of an organism. A gene can encode an expressed product, such as a polypeptide or a polynucleotide (e.g., tRNA). Alternatively, a gene may define a genomic location for a particular event/function, such as the binding of proteins and/or nucleic acids (e.g., phage attachment sites), wherein the gene does not encode an expressed product. Typically, a gene includes coding sequences, such as polypeptide encoding sequences, and non-coding sequences, such as promoter sequences, poly-adenlyation sequences, transcriptional regulatory sequences (e.g., enhancer sequences). Many eucaryotic genes have "exons" (coding sequences) interrupted by "introns" (non-coding sequences). In certain cases, a gene may share sequences with another gene(s) (e.g., overlapping genes).

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The term encompasses a gene. The boundaries of the coding sequence are determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence. Transcription and translation of coding sequences are typically regulated by "control elements" including, but not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

A "vector" is any moiety that is capable of transferring nucleic acid molecules (e.g., polynucleotide or gene sequences) to target cells (e.g., viral vectors, non-viral vectors, particulate carriers, and liposomes). Typically, "vector construct," "expression vector," and "gene transfer vector," mean any nucleic acid construct capable of directing the expression of a gene of interest and which can transfer gene sequences to target cells. Thus, the term includes cloning and expression vehicles, as well as viral vectors.

"Operably linked" refers to an arrangement of elements wherein the components so described are configured so as to perform their usual function. Thus, a given promoter that is operably linked to a coding sequence (e.g., a sequence encoding an antigen or interest) is capable of effecting the expression of the coding sequence when the regulatory proteins and proper enzymes are present. In some instances, certain control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

"Recombinant" as used herein to describe a nucleic acid molecule means a polynucleotide of genomic, cDNA, semi-synthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "re-combinant" as used with respect to a protein or polypeptide means a polypeptide produced by expression of a recombinant polynucleotide.

Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman (1981) *Advances in Applied Mathematics* 2:482–489. This algorithm can be applied to amino acid sequences by using the scoring matrix developed by Dayhoff, *Atlas of Protein Sequences and Structure*, M. O. Dayhoff ed., 5 suppl. 3:353–358, National Biomedical Research Foundation, Washington, D.C., USA, and normalized by Gribskov (1986) *Nucl. Acids Res.* 14(6):6745–6763. An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

Alternatively, homology can be determined by hybridization of polynucleotides under conditions which form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%–85%, preferably at least about 90%, and most preferably at least about 95%–98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. For example, stringent hybridization conditions can include 50% formamide, 5× Denhardt's Solution, 5×SSC, 0.1% SDS and 100 µg/ml denatured salmon sperm DNA and the washing conditions can include 2×SSC, 0.1% SDS at 37° C. followed by 1×SSC, 0.1% SDS at 68° C. Defining appropriate hybridization conditions is within the skill of the art. See, e.g., Sambrook et al., supra; *DNA Cloning*, supra; *Nucleic Acid Hybridization*, supra.

The term "vaccine composition" intends any pharmaceutical composition containing an antigen (particularly, as used herein the term refers to a composition containing a nucleic acid molecule having a sequence that encodes an antigen), which composition can be used to prevent or treat a disease or condition in a subject. Vaccine compositions may also contain one or more adjuvants. Typically a vaccine composition is used for the prophylaxis of a disease caused by a pathogen, however, the vaccine compositions of the present invention can also be used in a therapeutic context.

An "immunological response" or "immune response" against a selected agent, antigen or a composition of interest is the development in an individual of a humoral and/or a cellular immune response to molecules (e.g., antigen) present in the agent or composition of interest. For purposes of the present invention, a "humoral immune response" refers to an immune response mediated by antibody molecules, while a "cellular immune response" is one mediated by T-lymphocytes and/or other white blood cells.

Mammalian immune responses are understood to involve an immune cascade following one of two broad categories of response, characterized by the class of T helper cell which initiates the cascade. Thus, an immune response to a specific antigen may be characterized as a T helper 1 (Th1)-type or T helper 2 (Th2)-type response, depending on the types of cytokines that are released from antigen-specific T lymphocytes following antigen presentation. Th1 immune responses are generally characterized by the release of inflammatory cytokines, such as IL-2, interferon-gamma (IFN-γ), and tumor necrosis factor alpha (TNF-α), from the antigen-stimulated T helper cells. Th1 responses are also associated with strong cellular immunity (e.g., CTLs) and the production of IgG antibody subclasses that possess opsonizing and complement-fixing activity, such as IgG2a in the commonly used mouse model. On the other hand, Th2 immune responses are characterized by the release of noninflammatory cytokines, such as IL-4 and IL-10, following stimulation of antigen-specific T helper cells. The Th2 responses generally do not favor maximal CTL activity, but are associated with strong antibody responses, representing IgG subclasses such as IgG1 in the mouse, antibody classes that lack opsonizing and complement-fixing activity. In general, the antibody levels associated with Th2 responses are considerably stronger than those associated with Th1 responses.

The term "adjuvant" intends any material or composition capable of specifically or non-specifically altering, enhancing, directing, redirecting, potentiating or initiating an antigen-specific immune response. Thus, coadministration of an adjuvant and an antigen (e.g., as a vaccine composition) may result in a lower dose or fewer doses of antigen being necessary to achieve a desired immune response in the subject to which the antigen is administered. In certain embodiments of the invention, coadministration of an adjuvant with a nucleic acid encoding an antigen can redirect the immune response against the antigen, for example, where the immune response is redirected from a Th2-type to a Th1-type immune response, or vice versa. The effectiveness of an adjuvant can be determined by administering the adjuvant with a vaccine composition and vaccine composition controls to animals and comparing antibody titers and/or cellular-mediated immunity against the two using standard assays such as radioimmunoassay, ELISAs, CTL assays, and the like, well known in the art. Typically, in a vaccine composition, the adjuvant is a separate moiety from the antigen, although a single molecule can have both adjuvant and antigen properties (e.g., cholera toxin). For the purposes of the present invention, an adjuvant is used to either enhance the immune response to a specific antigen, e.g., when an adjuvant is coadministered with a vaccine composition, the resulting immune response is greater than the immune response elicited by an equivalent amount of the vaccine composition administered without the adjuvant, or the adjuvant is used to redirect the nature of the immune response. In addition, for the purposes of the present invention, an "effective amount" of an adjuvant will be that amount which enhances an immunological response to a coadministered antigen in a vaccine composition such that lower or fewer doses of the antigen are required to generate an efficient immune response, or an "effective amount" of an adjuvant will be that amount which is sufficient to bring about a shift or redirection of the immune response relative to the immune response to the antigen alone. An "adjuvant composition" intends any pharmaceutical composition containing an adjuvant.

An "immune shift adjuvant" is an adjuvant that is effective to alter or direct (re-direct) the nature of an immune response against a selected antigen receiving both the antigen and the immune shift adjuvant. The altering or redirecting is relative to the nature of the immune response that is directed against the antigen in the absence of the immune shift adjuvant. Thus, such adjuvants are used herein to shift the nature of an immune response elicited against a selected antigen (an antigen encoded by a nucleic acid sequence present in a genetic vaccine composition) to favour a Th1-type response in lieu of a Th2-type response, or to favour a Th2-type response in lieu of a Th1-type response. A number of known adjuvants can be used herein as immune shift adjuvant including, but not limited to a monophosphoryl lipid A (MPL) adjuvant. The ability of an adjuvant to serve as an immune shift adjuvant can be determined by assessing the nature of immune responses engendered by administration of the vaccine composition alone, and administration of the vaccine composition with the adjuvant. This assessment can involve a characterization or identification of the types of cytokines that are released from antigen-specific T lymphocytes following antigen presentation in an individual and/or the characterization or identification of the predominate IgG subclasses that are elicited by an antigen/adjuvant combination relative to antigen alone. All of these characterization or identifications are well within the skill of the ordinarily skilled artisan as directed by the present specification.

As used herein, the term "coadministered," such as when an adjuvant is "coadministered" with a nucleic acid encoding an antigen (e.g., a vaccine composition), intends either the simultaneous or concurrent administration of adjuvant and antigen, e.g., when the two are present in the same composition or administered in separate compositions at nearly the same time but at different sites, as well as the delivery of adjuvant and antigen in separate compositions at different times. For example, the adjuvant composition may be delivered prior to or subsequent to delivery of the antigen at the same or a different site. The timing between adjuvant and antigen deliveries can range from about several minutes apart, to several hours apart, to several days apart.

As used herein, the term "treatment" includes any of following: the prevention of infection or reinfection; the reduction or elimination of symptoms; and the reduction or complete elimination of a pathogen. Treatment may be effected prophylactically (prior to infection).

The terms "individual" and "subject" are used interchangeably herein to refer to any member of the subphylum cordata, including, without limitation, humans and other primates (including non-human primates such as chimpanzees and other apes and monkey species); farm animals such as cattle, sheep, pigs, goats and horses; domestic mammals such as dogs and cats; laboratory animals including rodents such as mice, rats and guinea pigs; birds (including domestic, wild and game birds such as chickens, turkeys and other gallinaceous birds, ducks, geese); fish; and the like. The terms do not denote a particular age. Thus, both adult and newborn individuals are intended to be covered. The methods described herein are intended for use in any of the above vertebrate species, since the immune systems of all of these vertebrates operate similarly.

B. General Methods

A basic premise of the present invention is the discovery that a non-DNA adjuvant can be incorporated into a nucleic acid-based vaccine composition (e.g., a DNA or genetic vaccine composition) and used to alter, enhance, direct or re-direct the nature of the immune response to an antigen in a treated individual. Compositions, which contain a combination of a nucleic acid molecule that includes a sequence encoding an antigen of interest, and an adjuvant which is in a form other than DNA, are administered directly into cells present in target tissue in an individual to be treated. It is preferred, but not necessary, that the composition be coated onto a core carrier particle which greatly facilitates the direct, intracellular delivery of the novel compositions. The adjuvant component of the composition is effective to enhance at least one aspect of an immune response elicited against the companion antigen. In some aspects of the invention, the adjuvant is selected to shift or re-direct the nature of the antigen-specific immune response relative to the antigen-specific immune response that is engendered in the absence of the coadministered adjuvant. In other aspects of the invention, the adjuvant is selected to enhance the T helper 1 (Th1) component of the antigen-specific immune response.

In one particular aspect of the invention, it has been found that the addition of an appropriate immune response shifting adjuvant to a DNA vaccine has the effect of stimulating and shifting the antigen-specific immune response elicited by the vaccine to favor a Th1 response in lieu of a Th2 response. One particular adjuvant that has been found to have this effect is monophosphoryl lipid A (MPL), although other adjuvants of similar effect have been identified. Such a shift of immune response in a DNA vaccine increases the efficacy of DNA vaccines to a variety of infectious disease, such as malaria.

Antigens

The nucleic acid molecules for the genetic vaccine component of the present compositions do not require elaborate preparation techniques. The most critical preparation step is then, quite clearly, the selection of an appropriate sequence that encodes a antigen of interest. The antigen is selected so that the immune response, when elicited, will provide some level of therapeutic effect to the vaccinated individual, for example some level of effective protection against a disease agent. In those embodiments where it is intended that the immune response from a DNA vaccine be modified to enhance the Th1 character of the immune response, the antigen encoded by the DNA in the vaccine will be selected with this effect in mind.

Thus, in general, the antigen will be selected with a particular delivery method, target tissue, and companion adjuvant in mind. For example, particle-mediated immunization of mice with vectors encoding influenza virus nucleoprotein antigen (NP), human carcino embryonic antigen (CEA), or *P. falciparum* CS antigen predictably results in the induction of antibody responses indicative of a Th2 response. On the other hand, immunization of mice with vectors encoding HIV proteins results in initially Th1-like responses that can be converted to Th2 responses with additional immunizations. Further, immunization with vectors encoding the hepatitis B virus (HBV) surface and core antigens results in a response that might be classified as Th0 due to equal representation of both of the major subclasses of IgG in the antigen-specific immune response. Thus, for certain infectious or parasitic diseases, it is possible that the immunological outcome following DNA vaccination will be appropriate for providing optimal protection, while for others, modulation or redirection of the immunological outcome is necessary to achieve an effective level of protection that is higher than that observed without the use of the adjuvant. For example, it is also possible that for certain infectious or parasitic diseases, the immunological responses, while significant in strength, may not be appropriate for providing optimal therapeutic effect, e.g., protection. In other words, the immune response may be quantitatively sufficient, but qualitatively insufficient. Such may be the case with malaria, in which prior vaccine data indicates that Th1 responses may be important, but where Th2 responses are elicited via DNA vaccination of the epidermis, when using a CS-encoding plasmid vector. Thus the effect of the type of adjuvant envisioned here may be not to enhance the quantitative level of immune response, but instead simply to redirect the immune response to enhance the Th1 component of that response.

Accordingly, for the nucleic acid component of the present compositions, a suitable promoter system will be operably linked sequence which encodes an antigen of interest. The antigen of interest will preferably be associated with a pathogen, such as a viral, bacterial or parasitic pathogen, or the antigen may be a tumor-specific antigen, a self-antigen or an allergen. The antigen may be a full length protein. Alternatively, the antigen may just consist essentially of a B-cell epitope or a T-cell epitope of an antigen.

Tumor-specific antigens include, but are not limited to, any of the various MAGEs (melanoma associated antigen E), including MAGE 1, MAGE 2, MAGE 3 (HLA-A1 peptide), MAGE 4, etc.; any of the various tyrosinases (HLA-A2 peptide); mutant ras; mutant p53; and p97 melanoma antigen. Other tumor-specific antigens include the Ras peptide and p53 peptide associated with advanced cancers, the HPV 16/18 and E6/E7 antigens associated with cervical cancers, MUC1-KLH antigen associated with breast carcinoma, CEA (carcinoembryonic antigen) associated with colorectal cancer, gp100 or MART1 antigens associated with melanoma, and the PSA antigen associated with prostate cancer. The p53 gene sequence is known (see e.g., Harris et al. (1986) *Mol. Cell. Biol.* 6:4650–4656) and is deposited with GenBank under Accession No. M14694.

Suitable viral antigens include, but are not limited to, antigens obtained or derived from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV). By way of example, the viral genomic sequence of HBV is known, as are methods for obtaining antigen-encoding sequences therefrom. See, e.g., Ganem et al. (1987) *Annu. Rev. Biochem.* 56:651–693; Hollinger, F. B. (1990) *Hepatitis B virus*, vol. II, pp. 2171–2235, in Fields et al. (eds), *Virology*, 2nd ed, Raven Press, New York, N.Y.; and Valenzuela et al. (1980) *The nucleotide Sequence of the Hepatitis B viral Genome and the Identification of the Major Viral Genes*, pp. 57–70, in Fields et al. (eds), *Animal Virus Genetics*, Academic Press, New York, N.Y.). The HBV genome encodes several viral proteins, including the large, middle and major surface antigen polypeptides, the X-gene polypeptide, and the core polypeptide. See, e.g., Yokosuka et al. (1986) *N. Engl. J. Med.* 315:1187–1192; Imazeki et al. (1987) *Hepatology* 7:753–757; Kaneko et al. (1988) *J. Virol.* 62:3979–3984; and Ou et al. (1990) *J. Virol.* 64:4578–4581. In like manner, the viral genomic sequence of HCV is known, as are methods for obtaining the sequence. See, e.g., International Publication Nos. WO 89/04669; WO 90/11089; and WO 90/14436. The HCV genome encodes several viral proteins, including E1 and E2. See, e.g., Houghton et al. (1991) *Hepatology* 14:381–388. The sequences encoding these HBV and HCV proteins, as well as antigenic fragments thereof, will find use in the present methods. Similarly, the coding sequence for the δ-antigen from HDV is known (see, e.g., U.S. Pat. No. 5,378,814).

In like manner, sequences encoding a wide variety of protein antigens from the herpesvirus family can be used in the present invention, including antigens derived or obtained from herpes simplex virus (HSV) types 1 and 2, such as HSV-1 and HSV-2 glycoproteins gB, gD and gH; antigens from varicella zoster virus (VZV), Epstein-Barr virus (EBV) and cytomegalovirus (CMV) including CMV gB and gH; and antigens from other human herpesviruses such as HHV6 and HHV7. (See, e.g. Chee et al. (1990) *Cytomegaloviruses* (J. K. McDougall, ed., Springer-Verlag, pp. 125–169; McGeoch et al. (1988) *J. Gen. Virol.* 69:1531–1574; U.S. Pat. No. 5,171,568; Baer et al. (1984) *Nature* 310:207–211; and Davison et al. (1986) *J. Gen. Virol.* 67:1759–1816.)

HIV antigens, such as the gp120 sequences for a multitude of HIV-1 and HIV-2 isolates, including members of the various genetic subtypes of HIV, are known and reported (see, e.g., Myers et al., Los Alamos Database, Los Alamos National Laboratory, Los Alamos, N. Mex. (1992); and Modrow et al. (1987) *J. Virol.* 61:570–578) and antigens derived from any of these isolates will find use in the present methods. Furthermore, the invention is equally applicable to other immunogenic moieties derived from any of the various HIV isolates, including any of the various envelope proteins such as gp160 and gp41, gag antigens such as p24gag and p55gag, as well as proteins derived from the pol, env, tat, vif rev, nef vpr, vpu and LTR regions of HIV.

Sequences encoding antigens derived or obtained from other viruses will also find use in the claimed methods, such as without limitation, sequences from members of the families Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Bunyaviridae; Arenaviridae; Retroviradae (e.g., HTLV-I; HTLV-II; HIV-1 (also known as HTLV- III, LAV, ARV, hTLR, etc.)), including but not limited to antigens from the isolates $HIV_{IIB}$, $HIV_{SF2}$, $HIV_{LAV}$, $HIV_{LAI}$, $HIV_{MN}$); HIV-$1_{CM235}$, HIV-$1_{US4}$; HIV-2, among others. See, e.g. Virology, 3rd Edition (W. K. Joklik ed. 1988); *Fundamental Virology,* 2nd Edition (B. N. Fields and D. M. Knipe, eds. 1991), for a description of these and other viruses.

Sequences encoding suitable bacterial and parasitic antigens are obtained or derived from known causative agents responsible for diseases such as Diptheria, Pertussis, Tetanus, Tuberculosis, Bacterial or Fungal Pneumonia, Cholera, Typhoid, Plague, Shigellosis or Salmonellosis, Legionaire's Disease, Lyme Disease, Leprosy, Malaria, Hookworm, Onchocerciasis, Schistosomiasis, Trypamasomialsis, Lesmaniasis, *Giardia*, Amoebiasis, Filariasis, *Borrelia*, and Trichinosis. Still further antigens can be obtained or derived from unconventional viruses or virus-like agents such as the causative agents of kuru, Creutzfeldt-Jakob disease (CJD), scrapie, transmissible mink encephalopathy, and chronic wasting diseases, or from proteinaceous infectious particles such as prions that are associated with mad cow disease.

Sequences encoding suitable allergens that may find use in the present invention include, but are not limited to, allergens from pollens, animal dander, grasses, molds, dusts, antibiotics, stinging insect venoms, and a variety of environmental, drug and food allergens. Common tree allergens include pollens from cottonwood, popular, ash, birch, maple, oak, elm, hickory, and pecan trees; common plant allergens include those from rye, ragweed, English plantain, sorreldock and pigweed; plant contact allergens include those from poison oak, poison ivy and nettles; common grass allergens include Timothy, Johnson, Bermuda, fescue and bluegrass allergens; common allergens can also be obtained from molds or fungi such as *Alternaria, Fusarium, Hormodendrum, Aspergillus, Micropolyspora, Mucor* and thermophilic actinomycetes; penicillin and tetracycline are common antibiotic allergens; epidermal allergens can be obtained from house or organic dusts (typically fungal in origin), from insects such as house mites (dermatphagoides pterosinyssis), or from animal sources such as feathers, and cat and dog dander; common food allergens include milk and cheese (diary), egg, wheat, nut (e.g., peanut), seafood (e.g., shellfish), pea, bean and gluten allergens; common drug allergens include local anesthetic and salicylate allergens; antibiotic allergens include penicillin and sulfonamide allergens; and common insect allergens include bee, wasp and ant venom, and cockroach calyx allergens. Particularly well characterized allergens include, but are not limited to, the major and cryptic epitopes of the Der p I allergen (Hoyne et al. (1994) *Immunology* 83190–195), bee venom phospholipase A2 (PLA) (Akdis et al. (1996) *J. Clin. Invest.* 98:1676–1683), birch pollen allergen Bet v 1 (Bauer et al. (1997) *Clin. Exp. Immunol.* 107:536–541), and the multi-epitopic recombinant grass allergen rKBG8.3 (Cao et al. (1997) *Immunology* 90:46–51). These and other suitable allergens are commercially available and/or can be readily prepared following known techniques.

The coding sequence for the antigen of interest can be obtained and/or prepared using known methods. For example, substantially pure antigen preparations can be obtained using standard molecular biological tools. That is, polynucleotide sequences coding for the above-described antigens can be obtained using recombinant methods, such as by screening cDNA and genomic libraries from cells expressing the gene, or by deriving the gene from a vector known to include the same. Furthermore, the desired sequence can be isolated directly from cells and tissues containing the same, using standard techniques, such as phenol extraction and PCR of cDNA or genomic DNA. See, e.g., Sambrook et al., supra, for a description of techniques used to obtain and isolate DNA. Polynucleotide sequences can also be produced synthetically, rather than cloned.

Yet another convenient method for isolating specific nucleic acid molecules is by the polymerase chain reaction (PCR). Mullis et al. (1987) *Methods Enzymol.* 155:335–350. This technique uses DNA polymerase, usually a thermostable DNA polymerase, to replicate a desired region of DNA. The region of DNA to be replicated is identified by oligonucleotides of specified sequence complementary to opposite ends and opposite strands of the desired DNA to prime the replication reaction. The product of the first round of replication is itself a template for subsequent replication, thus repeated successive cycles of replication result in geometric amplification of the DNA fragment delimited by the primer pair used.

Once the particular coding sequence of interest has been obtained, it can be operably linked to suitable control elements to provide an expressible nucleic acid molecule using standard cloning or molecular biology techniques. See, e.g., Edge (1981) *Nature* 292:756; Nambair et al. (1984) *Science* 223:1299; and Jay et al. (1984) *J. Biol. Chem.* 259:6311. The nucleic acid molecule can then be used per se or just as simply inserted into a suitable vector such as an expression plasmid or viral vector construct.

Thus, the nucleic acid molecules of the present invention typically comprise either a homologous or heterologous promoter sequence and other suitable control sequences. These other control sequences may comprise a terminator and or translation initiation sequence (e.g. GCCACCATGG (SEQ ID NO: 1) or GCCCCCATGG (SEQ ID NO: 2)) and/or translational stop codon (e.g. TAA, TAG or TGA) and/or polyadenylation signal and/or a RNA pause site. In addition, native or heterologous enhancer sequences for the promoter sequence may be present. Once constructed, the nucleic acid molecules can be administered using standard gene delivery protocols. Methods for gene delivery are known in the art. See, e.g., U.S. Pat. Nos. 5,399,346, 5,580,859, 5,589,466. Genes can be delivered either directly to a subject or, alternatively, delivered ex vivo, to cells derived from the subject and the cells reimplanted in the subject.

Adjuvants

The second component of the novel compositions of the present invention is the adjuvant component which can comprise and suitable adjuvant or combination of adjuvants. For example, suitable adjuvants include, without limitation, adjuvants formed from aluminum salts (alum), such as aluminum hydroxide, aluminum phosphate, aluminum sulfate, etc; oil-in-water and water-in-oil emulsion formulations, such as Complete Freunds Adjuvants (CFA) and Incomplete Freunds Adjuvant (IFA); mineral gels; block copolymers; Avridine™ lipid-amine; SEAM62; adjuvants formed from bacterial cell wall components such as adjuvants including lipopolysaccharides (e.g., lipid A or monophosphoryl lipid A (MPL), Imoto et al. (1985) Tet. Lett. 26: 1545–1548), trehalose dimycolate (TDM), and cell wall skeleton (CWS); heat shock protein or derivatives thereof; adjuvants derived from ADP-ribosylating bacterial toxins, including diphtheria toxin (DT), pertussis toxin (PT), cholera toxin (CT), the *E. coli* heat-labile toxins (LT1 and LT2), *Pseudomonas* endotoxin A, *Pseudomonas* exotoxin S, *B. cereus* exoenzyme, *B. sphaericus* toxin, *C. botulinum* C2 and C3 toxins, *C. limosum* exoenzyme, as well as toxins from *C. perfringens, C. spiriforma* and *C. difficile, staphy-* lococcus aureus EDIN, and ADP-ribosylating bacterial toxin mutants such as CRM197, a non-toxic diphtheria toxin mutant (see, e.g., Bixler et al. (1989) Adv. Exp. Med. Biol. 251:175; and Constantino et al. (1992) Vaccine); saponin adjuvants such as Quil A (U.S. Pat. No. 5,057,540), or particles generated from saponins such as ISCOMs (immunostimulating complexes); chemokines and cytokines, such as interleukins (e.g., IL-1 IL-2, IL-4, IL-5, IL-6, IL-7, IL-8, IL-12, etc.), interferons (e.g., gama interferon), macrophage colony stimulating factor (M-CSF), tumor necrosis factor (TNF), defensins 1 or 2, RANTES, MIP1-α and MIP-2, etc; muramyl peptides such as N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3 huydroxyphosphoryloxy)-ethylamine (MTP-PE) etc; adjuvants derived from the CpG family of molecules, CpG dinucleotides and synthetic oligonucleotides which comprise CpG motifs (see, e.g., Krieg et al. Nature (1995) 374:546, Medzhitov et al. (1997) Curr. Opin. Immunol. 9:4–9, and Davis et al. J. Immunol. (1998) 160:870–876) such as TCCATGACGTTCCTGATGCT (SEQ ID NO: 3) and ATC *C. limosum* exoenzyme GACTCTCGAGCGTTCTC (SEQ ID NO: 4); and synthetic adjuvants such as PCPP (Poly[di(carboxylatophenoxy)phosphazene) (Payne et al. Vaccines (1998) 16:92–98). Such adjuvants are commercially available from a number of distributors such as Accurate Chemicals; Ribi Immunechemicals, Hamilton, Mont.; GIBCO; Sigma, St. Louis, Mo.

Preferred adjuvants for use in the present compositions are those that are at least partially soluble in ethanol. A particularly preferred class of adjuvants for use herein are those classified as "saponins," that is, adjuvants originating from saponin producing plants of the genera *Quillaja, Saponaria*, or *Gypsophilia*. Saponins are glycosidic natural plant products, composed of a ring structure (the aglycone) to which is attached one or more sugar chains. The aglycone can be asteroid, triterpenoid or a steroidalalkaloid and the number of sugar attached to the glycosidic bonds can vary greatly. The most common saponins used as pharmaceutical adjuvants are the triterpene glycosides extracted from the South American tree *Quillaja saponaria* and are referred to as Quil A (see e.g., U.S. Pat. Nos. 5,688,772; 5,057,540; and 4,432,969; and International Publication No. WO 88/09336, published 1 Dec. 1988), the active component of which is termed QS-21. Another preferred adjuvant is a muramyl dipeptide analog termed "GMTP-N-DPG" (N-acetylglucosaminyl-N-acetylmuramyl-L-alanyl-D-isoglutamyl-L-alanyl-dipalmitoylpropylamide). See Fast et al. (1997) *Vaccine* 15:1748–1752.

Several adjuvants are preferred for use as an immune shift adjuvant in the present invention. The critical attribute of such an adjuvant is that it tend to redirect the elicited immune response in a particular desired direction relative to use of the antigen-encoding DNA by itself. It is particularly desirable if the adjuvant has the attribute of directing or shifting the immune response toward Th1 as opposed to Th2 responses. Since all immune responses to an antigen are complex, and many if not all immune responses involve elements of both Th1 and Th2 responses, it is not practical to seek total response re-direction. Instead, what is contemplated is a relative shift of type of immune response, for example by using an adjuvant to enhance a Th1 type response. For example, where it has been found that a particular antigen produces a predominantly Th2 response, and a Th1 response is a more desired outcome, a shift in the direction of Th1 will show greater clinical efficacy from the vaccine. An immune shift adjuvant as described herein may or may not result in any increase in the total quantitative immune response in the individual, which is the result usually sought by the incorporation of adjuvants in vaccines. Instead, the immune shift adjuvant is intended to shift or re-direct the nature or quality of the immune response rather than its magnitude or quantity.

An example of an immune shift adjuvant which favors the Th1 response is monophosphoryl lipid A, or MPL available from Ribi Immunochemical Research, Inc. An example of an immune shift adjuvant which favors the Th2 response is 1,25-dihydroxy vitamin $D_3$. Other possible immune shift adjuvants include PPD, a purified protein derivative of *Bacillus calmette* guerin (BCG), trehalose dimycolate, and mycobacterial cell wall skeletal material.

The adjuvant may be present in the instant compositions individually or in a combination of two or more adjuvants. In this regard, combined adjuvants may have an additive or a synergistic effect in promoting or shifting an immune response. A synergistic effect is one where the result achieved by combining two or more adjuvants is greater than one would expect than by merely adding the result achieved with each adjuvant when administered individually.

Unfortunately, a majority of the above-referenced adjuvants are known to be highly toxic, and are thus generally considered too toxic for human use. It is for this reason that the only adjuvant currently approved for human usage is alum, an aluminum salt composition. Nevertheless, a number of the above adjuvants are commonly used in animals and thus suitable for numerous intended subjects, and several are undergoing preclinical and clinical studies for human use. However, it has been found that adjuvants which are generally considered too toxic for human use may be administered with a powder injection technique (such as the preferred particle-mediated delivery technique used herein) without concomitant toxicity problems. Without being bound by a particular theory, it appears that delivery of small amounts of adjuvants to the skin allows interaction with Langerhans cells in the epidermal layer and dendritic cells in the cutaneous layer of the skin. These cells are important in initiation and maintenance of an immune response. Thus, an enhanced adjuvant effect can be obtained by targeting delivery into or near such cells. Moreover, transdermal delivery of adjuvants in the practice of the invention may avoid toxicity problems because (1) the top layers of the skin are poorly vascularized, thus the amount of adjuvant entering the systemic circulation is reduced which reduces the toxic effect; (2) skin cells are constantly being sloughed, therefore residual adjuvant is eliminated rather than absorbed; and (3) substantially less adjuvant can be administered to produce a suitable adjuvant effect (as compared with adjuvant that is delivered using conventional techniques such as intramuscular injection).

Once selected, one or more adjuvant can be provided in a suitable pharmaceutical form for parenteral delivery, the preparation of which forms are well within the general skill of the art. See, e.g., Remington's Pharmaceutical Sciences (1990) Mack Publishing Company, Easton, Pa., 18th edition. Alternatively, the adjuvant can be rendered into particulate form as described in detail below. The adjuvant(s) will be present in the pharmaceutical form in an amount sufficient to bring about the desired effect, that is, either to enhance the mucosal response against the coadministered antigen of interest, and/or to direct a mucosal immune response against the antigen of interest. Generally about 0.1 μg to 1000 μg of adjuvant, more preferably about 1 μg to 500 μg of adjuvant, and more preferably about 5 μg to 300 μg of adjuvant will be effective to enhance an immune response of a given antigen. Thus, for example, for Quil A, doses in the range of about 0.5 to 50 μg, preferably about 1 to 25 μg, and more preferably about 5 to 20 μg, will find use with the present methods. For MPL, a dose in the range of about 1 to 250 μg, preferably about 20 to 150 μg, and more preferably about 40 to 75 μg, will find use with the present methods.

Doses for other adjuvants can readily be determined by one of skill in the art using routine methods. The amount to administer will depend on a number of factors including the coadministered antigen, as well as the ability of the adjuvant to act as stimulator of an immune response or to act as an immune shift adjuvant.

Preparation of the Compositions

Once obtained, the nucleic acid molecule encoding the antigen of interest and, in most embodiments, the selected adjuvant can be formulated together as a single pharmaceutical preparation. In other embodiments, the adjuvant can be prepared in any pharmaceutically acceptable form, for example as a liquid solution or suspension (suitable for injection or topical administration) or as a cream, emulsion, ointment, gel or other suitable topical pharmaceutical form. For example, the antigen-encoding sequence and/or the adjuvant can be combined with one or more pharmaceutically acceptable excipient or vehicle to provide a vaccine, adjuvant or adjuvanted genetic vaccine composition. Auxiliary substances, such as wetting or emulsifying agents, pH buffering substances, and the like, may be present in the excipient or vehicle. These excipients, vehicles and auxiliary substances are generally pharmaceutical agents that do not themselves induce an immune response in the individual receiving the composition, and which may be administered without undue toxicity. Pharmaceutically acceptable excipients include, but are not limited to, liquids such as water, saline, polyethyleneglycol, hyaluronic acid, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. It is also contemplated, although not required, that the composition may contain a pharmaceutically acceptable carrier that serves as a stabilizer, particularly for nucleic acids and/or peptide, protein or other like adjuvants. Examples of suitable carriers that also act as stabilizers for nucleic acids and peptides include, without limitation, pharmaceutical grades of dextrose, sucrose, lactose, trehalose, mannitol, sorbitol, inositol, dextran, and the like. Other suitable carriers include, again without limitation, starch, cellulose, sodium or calcium phosphates, citric acid, tartaric acid, glycine, high molecular weight polyethylene glycols (PEGs), and combination thereof. A thorough discussion of pharmaceutically acceptable excipients, carriers, stabilizers and other auxiliary substances is available in REMINGTON'S PHARMACEUTICAL SCIENCES (Mack Pub. Co., N.J. 1991), incorporated herein by reference.

Since the vaccine compositions of the present invention are intended to be delivered directly into cells present in a target site, particle-mediated delivery is the preferred method for administering the compositions in the practice of the invention. Accordingly, the nucleic acid molecules and/or adjuvants can be coated onto core carrier particles that are suitable for intracellular delivery, e.g., gold or tungsten. Particle-mediated methods for delivering such vaccine preparations are known in the art. More particularly, once prepared and suitably purified, the nucleic acid molecules encoding antigens and/or adjuvants can be coated onto carrier particles (e.g., ballistic core carriers) using a variety of techniques known in the art. Carrier particles are selected from materials which have a suitable density in the range of particle sizes typically used for intracellular delivery from a gene gun device. The optimum carrier particle size will, of course, depend on the diameter of the target cells.

Delivery using particle-mediated techniques is preferred for several reasons. One very important reason is that this technique for gene delivery into mammals has been shown to have the same level of efficacy in all mammalian systems tested so far. The significance of this fact is that data for animal models is more directly applicable and transferable to treatment of humans than is possible with other techniques, such as intramuscular gene delivery which has been shown to have a dramatically different efficacy in rodents. Particle-mediated delivery devices generally accelerate the genetic material into the animal through the use of an adjustable propulsive force, either an electric spark discharge or a discharge of compressed gas, thus making it possible to easily select the target tissues into which the nucleic acid vaccine compositions is to be delivered.

In accordance with established particle-mediated delivery techniques, the genetic material to be delivered can be prepared in aqueous solution and then precipitated onto small biologically inert core carrier particles. Any suitable carrier particle can be used, for example, particles formed from polymers or metals (e.g., tungsten, gold, platinum and iridium); however, tungsten and gold carrier particles are preferred. Tungsten particles are readily available in average sized of 0.5 to 2.0 μm in diameter. Although such particles have optimal density for use in particle-mediated delivery methods, and allow highly efficient coating with DNA, tungsten may potentially be toxic to certain cell types. Gold particles or microcrystalline gold (e.g., gold powder A1570, available from Engelhard Corp., East Newark, N.J.) will also find use with the present methods. Gold particles provide uniformity in size (available from Alpha Chemicals in particle sizes of 1–3 μm, or available from Degussa, South Plainfield, N.J. in a range of particle sizes including 0.95 μm) and reduced toxicity. Microcrystalline gold provides a diverse particle size distribution, typically in the range of 0.5–5 μm. However, the irregular surface area of microcrystalline gold provides for highly efficient coating with nucleic acids, antigens and adjuvants. Gold particle having a nominal size of about 0.1 μm to about 10 μm can be used herein.

A number of methods are known and have been described for coating or precipitating DNA or RNA onto gold or tungsten particles. Such methods generally combine a predetermined amount of gold or tungsten with plasmid DNA, $CaCl_2$ and spermidine. The resulting solution is vortexed continually during the coating procedure to ensure uniformity of the reaction mixture. After precipitation of the nucleic acid, the coated particles can be transferred to suitable membranes and allowed to dry prior to use, coated onto surfaces of a sample module, cartridge or cassette, or loaded into a delivery cassette for use in particle-mediated delivery devices (e.g., gene gun instruments).

Peptide adjuvants can be attached to the same or to a different supply of core carrier particles by simply mixing the two components in an empirically determined ratio, by ammonium sulfate precipitation or other solvent precipitation methods familiar to those skilled in the art, or by chemical coupling of the peptide to the carrier particle. The coupling of L-cysteine residues to gold has been previously described (Brown et al. (1980) *Chemical Society Reviews* 9:271–311). Other methods include, for example, dissolving the peptide in absolute ethanol, water, or an alcohol/water mixture, adding the solution to a quantity of carrier particles, and then drying the mixture under a stream of air or nitrogen gas while vortexing. Alternatively, peptides can be dried onto carrier particles by centrifugation under vacuum. Once dried, the coated particles can be resuspended in a suitable solvent (e.g., ethyl acetate or acetone), and triturated (e.g., by sonication) to provide a substantially uniform suspension.

In one embodiment, the invention entails the use of an MPL adjuvant in a genetic vaccine composition, MPL being a complex lipid molecule. While certain compounds can simply be mixed into the aqueous nucleic acid (e.g., DNA) preparation prior to coating onto the carrier particles, and while this may work in the case of MPL, MPL or other ethanol-soluble compounds can simply be added to the ethanol solution that is typically used to suspend the DNA-coated gold particles. Even though the ethanol is ultimately evaporated from the DNA-coated gold particles, sufficient adjuvant (e.g., MPL which is non-volatile) remains after evaporation. These same general techniques can be used with other classes of biological materials in the particle-mediated gene delivery process, such as adjuvants formed from non-protein hormones, vitamins, or analogs thereof.

Although it is convenient to pre-package the adjuvant with the DNA on the carrier particles, it has also been found that the adjuvant can be effective even if delivered separately from the genetic material. For example, in epidermal delivery via a particle-mediated technique, the adjuvant can simply be applied topically to the area to be treated with the genetic vaccine. It is not known if the particles carry the adjuvant to the site of gene expression or if the adjuvant is effective simply because it diffuses to the site of gene delivery. For particle-mediated gene delivery, the difference is not critical. The adjuvant can either be delivered with the genes or applied separately topically, for example by swab.

Particle-mediated delivery techniques permit the vaccine compositions to be directed to any target tissue type or category in the body. However, it is most convenient to deliver carrier particles carrying DNA into the epidermis. Conveniently, the epidermis has proven to be an especially desirable location for the delivery of DNA vaccines. It has already been demonstrated that a quantitatively higher immune response to a genetic vaccine can be elicited in the epidermis as compared with other possible target tissues. The vigorous immune response elicited in gene delivery into the epidermis may be due to immune cells, such as Langerhans cells or other antigen-presenting cells, which regularly infuse into the epidermal layer of the skin in search of antigenic targets.

Accordingly, following their formation, carrier particles coated with antigen and/or adjuvant preparations are delivered to the target skin site using a particle-mediated delivery technique. Various particle acceleration devices suitable for particle-mediated delivery are known in the art, and are all suited for use in the practice of the invention. Current device designs employ an explosive, electric or gaseous discharge to propel the coated carrier particles toward target cells. The coated carrier particles can themselves be releasably attached to a movable carrier sheet, or removably attached to a surface along which a gas stream passes, lifting the particles from the surface and accelerating them toward the target. An example of a gaseous discharge device is described in U.S. Pat. No. 5,204,253. An explosive-type device is described in U.S. Pat. No. 4,945,050. One example of a helium discharge-type particle acceleration apparatus is the PowderJect® XR instrument (PowderJect Vaccines, Inc., Madison), WI, which instrument is described in U.S. Pat. No. 5,120,657. An electric discharge apparatus suitable for use herein is described in U.S. Pat. No. 5,149,655. The disclosure of all of these patents is incorporated herein by reference.

Single dosages of the coated carrier particles can be provided in a suitable container, for example, provided in a cartridge that comprises a length of tubing that contains a dose of the particles coated on an inner surface thereof. Methods for preparing such containers are described in commonly owned U.S. Pat. Nos. 5,733,600 and 5,780,100, the disclosures of which are incorporated herein by reference.

The particle compositions or coated particles are administered to the individual in a manner compatible with the dosage formulation, and in an amount that will be effective for the purposes of the invention. The amount of the composition to be delivered (e.g., about 0.01 µg to 10 mg, more preferably 1 to 50 µg of the antigen sequence, depends upon the individual to be tested and the particular antigen(s) or allergen(s) being administered. The exact amount necessary will vary depending on the age and general condition of the individual to be treated, and an appropriate effective amount can be readily determined by one of skill in the art upon reading the instant specification.

Administration and Dosage Schedules

The vaccine compositions (containing the antigen-encoding sequence and/or adjuvant) are administered to the subject in a manner compatible with the dosage formulation, and in amounts effective to bring about a desired mucosal immune response. The amount of the antigen to be delivered per administration is, in the case of nucleic acid molecules encoding an antigen, generally in the range of from about 0.001 µg to 10 mg, and preferably about 0.01 to 5000 µg of nucleic acid molecule per dose (generally in the range of from 0.5 µg/kg to 100 µg/kg of nucleic acid molecule per dose). The exact amount will, of course, depend upon both the subject and the condition to be treated or prevented. More particularly, the exact amount necessary will vary depending on the age and general condition of the individual, and the particular antigen(s) and adjuvant(s) selected, as well as other factors. An appropriate effective amount can be readily determined by one of skill in the art upon reading the instant specification and/or can be determined through routine trials.

Dosage treatment may be a single dose schedule or a multiple dose schedule. For vaccine compositions, a multiple dose schedule is one in which a primary course of vaccination may be with 1–10 separate doses, followed by other doses given at subsequent time intervals, chosen to maintain and/or reinforce the immune response, for example at 1–4 months for a second dose, and if needed, a subsequent dose(s) after several months. The dosage regimen will also, at least in part, be determined by the need of the subject and be dependant on the judgment of the practitioner. Furthermore, if prevention of disease is desired, the compositions are generally administered prior to primary infection with the pathogen of interest. If treatment is desired, e.g., the reduction of symptoms or recurrences, the compositions are generally administered subsequent to primary infection.

C. Examples

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Re-Direction of an Immune Response to CEA Using Particle-Mediated Delivery Technique In order to demonstrate the influence of the MPL adjuvant on the immune response for a naked DNA vaccine, the following study was carried out. The adjuvant and the nucleic acid molecule containing the sequence encoding the antigen of interest were co-administered via particle-mediated delivery using a gene gun. The particular antigen used for this example was the human carcino embryonic antigen ("CEA"), a human tumor antigen widely used in experiments investigating cancer therapeutic treatments. Previous work had revealed that when a gene encoding CEA was delivered by particle-mediated delivery into mice, a type Th2 immune response was dominant, as indicated by a predominance of IgG1 in the serum antibody titer of the animal. Without an adjuvant, Th2 type CEA-specific antibodies (IgG1) are detected at levels more than twenty-fold higher than the levels of Th1 type CEA-specific antibodies (IgG2a) in Balb/c mice. The work performed herein was used to demonstrate that the Th2 immune response could be redirected towards a Th1 response through the use of an immune shift adjuvant.

For this protocol, a plasmid construct containing a coding region for the CEA antigen under the control of the cytomegalovirus immediate early promoter (CMV) with the CMV intron A between the promoter and the coding region was used. To form the composition, 64 µg of the plasmid, which was designated WRG7083, in 120 µL of water was added to 32 milligrams of 0.9 micron gold beads in an Eppendorf tube, i.e., 2 µg DNA/mg gold. Next, 13.5 µL of ammonium acetate solution and 135 µL of isopropanol were added, and the tube was vortexed briefly. The mixture was incubated for 15 minutes at −20° C. to precipitate the DNA onto the gold. The DNA coated beads were pelleted by a ten second spin and the supernatants were removed. The gold/DNA pellets were washed four times by vortexing in 1 mL ethanol, microfuging ten seconds, and removing supernatants. After the final wash, the DNA coated gold carrier particles were resuspended in 1.14 mL ethanol, so that each 250 µL of the ethanol suspension contained 7 mg of gold carrier particles with 2 µg of DNA per mg of gold.

Separately, a 1 mg/mL solution of MPL in ethanol was prepared and used as an MPL stock solution. Each of the following solutions were then prepared:

(0 MPL)—250 µL carrier particle suspension, 750 µL additional ethanol, and 0 µL MPL stock.

(0.05 mg/mL MPL)—250 µL carrier particle suspension, 750 µL additional ethanol, and 50 µL of MPL stock.

(0.2 mg/mL MPL)—250 µL carrier particle suspension, 750 µL additional ethanol, and 200 µL of MPL stock.

(0.5 mg/mL MPL)—250 µL carrier particle suspension, 750 µL additional ethanol, and 500 µL of MPL stock.

(1 mg/mL MPL)—250 µL carrier particle suspension with ethanol removed by centrifugation and replaced with MPL stock solution.

Each preparation was sonicated for ten seconds in a bath sonicator to generate a uniform gold carrier particle suspension in the ethanol.

The particle-mediated transfer described here was performed using a gene delivery instrument powered by compressed gas. This instrument was obtained from Agracetus, Inc. and termed the ACCELL® device, and substantially the same instrument can currently be obtained from PowderJect Vaccines, Inc. and is termed the PowderJect™ XR device. This general style of the instrument, which is described in PCT patent application PCT/US95/00780 and U.S. Pat. Nos. 5,865,796 and 5,584,807, the disclosures of which are hereby incorporated by reference, is constructed so that the DNA-coated carrier particles are placed, or coated, themselves onto the interior of a cylindrical particle carrier. For this carrier, cylindrical sections of Tefzel™ tubing were used. Using a syringe fitted with an adaptor made for this purpose, the above suspensions were each drawn into a 30 inch length of Tefzel™ tubing, one milliliter (7 mg of DNA coated gold particles) of each suspension filling a 7 inch length of the tubing, yielding a nominal distribution of 1 mg of DNA-coated gold carrier particles, with or without MPL, per inch of tubing. The tubing was transferred to a fixture which held the tubing in a linear horizontal configuration. After the carrier particles were allowed a moment to visibly settle, excess ethanol was drained from the tubing from one end and the tube was rotated for thirty seconds to distribute the carrier particles more evenly around the interior of the cylindrical tubing. The residual ethanol was then removed by passing nitrogen through the tubing for three minutes. The tubing was cut into sections, each of which was ½ inch in length. Each tube section was used as one charge of dose for the acceleration device, which released a jet of compressed helium gas through the interior of the tubing sections to pick up the carrier particles from the tubing and carry them onward toward the experimental subject.

The model animals were six-to-eight week old Balb/c mice (Harlan/Sprague/Dawley, Indianapolis Ind.), which had been anesthetized and had their abdominal hair clipped. At each of two adjacent sites on the abdomen of each animal, a single dose of DNA-coated carrier particles was delivered into the epidermis by a helium charge having a pressure of 400 psi. Thus each site received 1 µg of DNA on 0.5 mg gold carrier particles, with varying amounts of MPL, and each animal having two sites.

In a parallel experiment, the MPL stock was applied directly onto the skin of the treatments sites on the animal by swabbing prior to gene delivery. This was done by swabbing on the abdomen of the animal with a cotton applicator dipped into the MPL stock solution, after which the ethanol was allowed to evaporate for 10 seconds prior to delivery of the DNA-coated carrier particles at a corresponding dosage.

Four weeks after the treatment, sera samples were obtained from the immunized animals and CEA-specific antibodies (IgG and $IgG_{2a}$) were quantified using an ELISA kit from Southern Biotech. By comparing to standard immunoglobulin isotypes of known concentration, quantification of the types of CEA-specific immunoglobulins was performed.

The results of the study are depicted in FIG. 1. As can be seen, the three mice subjected to each of the dosage levels of the adjuvant of genetic vaccine and the adjuvant are represented by a single bar in the graph. On the left edge of the graph, the three bars represent the animals which received no MPL in their dosages, and the immune responses for those animals, as can be seen, were predominantly Th2-like, with an average of 27.5 times more IgG1 type antibodies as compared to IgG2a antibodies. The greatest change in the nature of the immunological response in the treated animals was at a rate of 0.2 mg/mL MPL, where the ratio of IgG1 to IgG2a had been reduced to 4.5. When MPL was swabbed on the animals, as indicated in the rightmost bars in FIG. 1, the results were comparable to the 0.2 mg/mL gene gun delivery method, with the ratio of IgG1 to IgG2a being about 4.0. The other MPL dosages showed variation in the level of re-direction of the immune response, but all clearly showed a more robust $IgG_{2a}$ response than can could be obtained with the genetic vaccine alone without the adjuvant. These results demonstrate that the use of the MPL adjuvant does indeed alter the nature of the immunological response to the genetic vaccine by shifting the response in favor of a Th1-type antibody production.

The studies of Examples 2–5, described herein below, were carried out to assess the adjuvant effect provided by intracellular coadministration of various antigen-encoding sequences with a Quil A adjuvant. In each study, DNA molecules containing sequences that encode viral antigens were combined with the Quil A adjuvant and coated onto gold particles in order to provide exemplary compositions according the present invention. The coated particles were administered to animal subjects, and the ability of the compositions to elicit antigen-specific Th, CTL and antibody responses was compared against extracellular intradermal or subcutaneous administration of the Quil A adjuvant immediately before DNA delivery. In each of the studies, the following general techniques were used.

Coating the Core Carrier Particles: Appropriate weights of gold particles were weighted directly into 1.5 mL Eppendorf tubes. 400–500 µL of a 0.05M spermidine was then added, and clumps of gold in the gold/spermidine solution were broken-up using a water bath sonicator for 3–5 seconds. DNA stock solution, containing the relevant DNA plasmid molecule, was added to the gold/spermidine solution to result in a bead loading rate of 2.0 µg DNA/mg Au, and the tubes were capped and inverted to mix, then vortexed briefly. After adjusting the vortexer speed down, and while vortexing gently, a volume of 10% $CaCl_2$ was added dropwise to an amount equal to the volume of spermidine added to the dry gold. Once the entire volume of $CaCl_2$ was added, the resultant solution was vortexed at high speed for about 5 seconds. The solution was then allowed to precipitate at room temperature for at least 10 minutes. Meanwhile, a polyvinylpyrrolidone (PVP)/ethanol stock solution was formed at a concentration of 0.03 mg PVP/mL EtOH. After the ten minute precipitation, the tubes were centrifuged briefly (10–15 seconds) to pellet all of the gold. The supernatant was aspirated, and the tubes were "raked" across an Eppendorf rack to loosen the gold pellet. 800 µL of EtOH was added, and the tubes were inverted several times to wash the DNA-coated gold. This step was repeated twice, after which the tubes were again centrifuged and the supernatant aspirated. The washed DNA-coated gold particles were then added to the PVP stock solution, and 50 µg of Quil A was added to the PVP-DNA-coated gold particle solution with sonication for 3 seconds. The resulting particles, which were coated with the DNA+ Quil A vaccine composition were then loaded into lengths of Tefzel™ tubing as described above in Example 1.

Mouse ELISPOT Assays: The materials and reagents were as follows. Coating antibodies included Rat anti-mouse IFN-γ Ab, Rat anti-mouse IL-4 AB or Rat anti-mouse IL-5 Ab (Pharmigen); detecting antibodies included Biotinylated rat anti-mouse IFN-γ, Biotinylated rat anti-mouse IL-4 or Biotinylated rat anti-mouse IL-5 (Pharmingen); sterile-filtered carbonate buffer pH 9.6 (Pierce), 96 well ELISPOT plates (Millipore), sterile 1× phosphate buffered saline (PBS, Gibco), streptavidin alkaline phosphatase conjugate (Mabtech); Alkaline phosphatase substrate kit (BioRad), and RPMI-10% FCS cell culture medium (Sigma). Cell stimulation was carried out as follows. For T-Helper Cell Cytokine Release, splenocytes from the vaccinated animals were cultured at $6 \times 10^6$ cells/mL in RPMI-10% FCS supplemented with sodium pyruvate and non-essential amino acids. One mL of cells were transferred to each well of a 24 well plate and, for each subject, one well=media only (for background control), and one well=antigen of choice or Class II peptide of choice. The plates were then incubated in a tissue culture incubator for 3 days. For CTL Precursor IFN-γ Release, splenocytes from the vaccinated animals were cultured at $6 \times 10^6$ cells/mL in RPMI-10% FCS supplemented with sodium pyruvate and non-essential amino acids. One mL of cells were transferred to each well of a 24 well plate and the plate was incubated for 2 days, after which CTL peptide was added to peptide wells. For each subject, one well=media only, one well=CTL peptide of choice at $10^{-5}$M, and one well=irrelevant CTL peptide. The plates were then incubated for an additional 24 hours after addition of peptide and prior to plating cells into ELISPOT plate.

Coating and blocking of the ELISPOT plates was carried out as follows. The ELISPOT plates were coated one day prior to plating cells using 50 µL per well of 15 µg/mL coating antibody in sterile carbonate buffer, pH 9.6. The coated plates were incubated overnight at 4° C., after which they were washed six times with 100 µL PBS to remove unbound coating Ab, and then gently blotted. Each well was blocked using 200 µL RPMI-10% FCS for 1–2 hours in a tissue culture incubator at room temperature. All blocking media was removed immediately prior to plating the cells. The cells were plated as follows. After 3 days, cells and supernatant were collected from each well and transferred to a 15 mL conical tube. The cells were spun down in a centrifuge to collect supernatant which was then stored at −80° C. until used in cytokine ELISA analyses. The pelleted cells were resuspended in 2–5 mL media, and then brought to a final concentration of $1 \times 10^7$/mL. The cells were added to the ELISPOT wells at $1 \times 10^6$/well.

The ELISPOT plates were developed as follows. The cells were flicked out and the plates washed two times with PBS using a squirt bottle. The wells were washed with DI water (leaving the water in the wells for a few minutes to lyse the remaining cells), and the plates were washed two more times. Detection antibody was diluted to 1 µg/mL in sterile PBS and then added at 50 µL/well and incubated for 2 hours at room temperature. The plates were washed five times with PBS, and 50 µL strepavidin alkaline phosphatase conjugate (diluted 1:1000 in PBS) and the plates were incubated at room temperature for 2 hours. The plates were then washed five times with PBS, and 50 µL of chromogenic alkaline phosphatase substrate was added and the plates allowed to incubate at room temperature until dark spots emerge (about 2 hours). The color reaction was stopped by washing three times with 200 µL of tap water, the plates allowed to air dry, and the spots counted under a dissecting microscope (40×).

Mouse Peptide-Pulsed CTL Assays: The materials and reagents were as follows. RPMI-10 Media (500 mL RPMI 1640 with L-glutamine and Hepes, 55 mL heat-inactivated fetal bovine serum (FBS), 0.5 mL gentamycin, 5.5 mL antibiotics antimycolic solution); Sensitization Media ("SM") without IL-2 (500 mL RPMI-10, 5.0 mL 100 mM Na Pyruvate, 5.0 mL 100× nonessential amino acids); and SM with IL-2 (SM with final concentration of 20 U/mL recombinant rat IL-2); CTL epitope peptide (peptide dissolved in tissue culture grade DMSO to stock concentration of $10^{-2}$M); ACK lysis buffer (BioWhittaker); recombinant rat IL-2 (Collaborative); Mitomycin C C (Aldrich dissolved in sterile PBS to obtain 500 μg/mL stock solution; 50 mL conical tubes (Falcon), nylon mesh strainer cup inserts (Falcon); $^{51}$Chromium and Lumaplates (Packard).

For peptide-pulsed stimulators, naive syngeneic spleens are provided (approx. $1.2 \times 10^7$ stimulators/mouse) by collecting spleens and grinding by pressing between two autoclaved frosted slides to break up the sac and release the cells into a small petri dish. Cell clumps are broken up by pipetting the cells up and down with a 3 mL transfer pipet, and the resulting cell suspension is passed through a 70 μm nylon cell strainer into a 50 mL conical tube using 5–10 mL RPMI-10 media to wash the cells through. The recovered splenocytes are spun at 1500 rpm for 5 minutes to pellet, and the supernatant discarded. The RBCs were lysed by resuspending the splenocytes in 5 mL ACK lysis buffer for 1–2 minutes, after which the cells were washed twice with 20 mL unsupplemented RPMI and once with RPMI-10. The cells were then resuspended at approximately $1 \times 10^7$ cells/mL. The stimulators were treated with mitomycin C (for each 10 mL cells, 500 μL of 0.5 mg/mL mitomycin C was added), and the cells were incubated with the mitomycin C for 25–45 minutes at 37° C., 5% $CO_2$. After treatment, the cells were washed twice with unsupplemented RPMI and once with RPMI-10. The washed cells were resuspended to $2 \times 10^6$ cells/mL in SM with 20 U/mL rat IL-2, and the stock CTL epitope peptide added. The stimulator cells were dispensed at a ratio of 3/1 responder/stimulator into 24-well plates and incubated overnight at 37° C., 5% $CO_2$.

The in vitro stimulation of responder cells was carried out as follows. Spleens were collected from vaccinated and control mice, and responder splenocytes were isolated by grinding the spleens as described above. RBCs were lysed with 5 mL ACK lysis buffer for 2–3 minutes, and the cells were washed two times with 20 mL unsupplemented RPMI and once with RPMI-10. The splenocytes were then resuspended at $6 \times 10^6$ cells/mL in SM without IL-2. For each mouse, 1 mL of splenocytes were dispensed into each well of a 24-well plate containing 1 mL of the $2 \times 10^6$ cells/mL peptide-pulsed stimulator cells described above in SM with IL-2 (final concentration of IL-2 was 10 U/mL), and the plates incubated at 37° C., 5% $CO_2$. for 5–7 days.

CTL $^{51}$Chromium Release Assay: For peptide-specific lysis, the following techniques were used. Log-phase syngeneic target cells were plated in 96 well plates at approximately 30,000 targets/well. An appropriate amount of target cells were pelleted in conical tubes and resuspended in 20 μL heat-inactivated FBS. 100–200 μL of $^{51}$Cr (sodium chromate) was added to each pellet, mixed well, then incubated for 1 hour at 37° C. The cells were then washed four times with 6–10 mL RPMI-10 per pellet, and then resuspended at $3 \times 10^5$ cells/mL in RPMI-10. For peptide-pulsed targets, an appropriate amount of the stock Ctl epitope peptide was added to reach a final optimal peptide concentration (approximately $10^{-5}$M). Target cells were allowed to pulse with the peptides for at least 30 minutes (at 37° C.) prior to plating with the effector cells.

After 5–7 days of in vitro stimulation, effector splenocytes were collected from the 24-well plates and the cells from each mouse were pooled in 15 mL conical tubes, and then resuspended at $1.5 \times 10^7$ cells/mL. For plating, splenocytes from each mouse were plated at 50, 17, 5.6 and 1.9 effector/ target ratios. After dilutions, 100 μL of the $^{51}$Cr-labeled targets were added to each well. The plates were spun briefly and then incubated 4–6 hours at 37° C. Lysis was measured against both peptide-pulsed and unpulsed control targets for each mouse.

For nonspecific lysis, the same protocol was followed except that 100 μL of unpulsed targets were also plated. After a 4–6 hour incubation, the plates were spun to pellet the cells and lysed. 25 μL of the supernatant was then transferred to Lumaplates and allowed to dry for 2 hour or overnight. The plates were sealed and counted using a standard program for $^{51}$Cr-solid. To calculate % Lysis, (test cpm–spont. cpm) was divided by (max. cpm–spont. cpm) and multiplied by 100. To obtain % specific lysis, the % lysis of unpulsed targets was subtracted from the % lysis of peptide-pulsed targets.

ELISA: Antibody response to the various vaccine compositions was determined by a standard ELISA procedure. More particularly, medium binding plates (Costar) were coated with 100 μL/well with a 1 μg/mL antigen stock solution (in PBS) and incubated overnight at 4° C. The antigen solution was aspirated and the plates blocked with 5% dry milk/PBS for at least one hour at room temperature. The plates were washed three times with wash buffer (10 mM TBS/0.1% Brij-35), and 100 μL of sample serum added and incubated for two hours at room temperature (dilution buffer: 2% dry milk/PBS/0.05% Tween-20). The plates were washed three times and incubated with biotin-labelled goat antibodies specific for mouse immunoglobulin IgG or specific IgG subclasses for 1 hr at room temperature. Following three additional washes, the ELISA plates were incubated with strepavidin-horseradish peroxidase conjugates for 1 hr at room temperature. Finally, plates were washed and developed with TMB substrate (kit from Bio-Rad, Richmond, Calif.) and allowed to develop for 30 minutes. Reactions were stopped with 1N $H_2SO_4$, and the plates read at A450. Mean background absorbance was determined by wells that received all reagents except for test sera.

Example 2

Intracellular Coadministration of Quil A with DNA on Gold Beads to Enhance an Influenza NP-Specific Immune Response In order to determine whether coadministration of a composition containing a DNA vaccine vector that encodes the influenza NP antigen and Quil A adjuvant directly into cells can enhance an antigen-specific immune response, the following study was carried out. Experimental groups of Balb/c mice were set up as follows: (Group 1) 3 control mice receiving gold beads coated with irrelevant DNA via the PowderJect™ XR particle-mediated delivery device; (Group 2) 3 mice receiving gold beads coated with the NP DNA vector only via the PowderJect™ XR device; (Group 3) 4 mice receiving gold beads coated with the NP DNA vector only via the PowderJect™ XR device and inoculated with trehalose or saline prior to DNA administration; (Group 4) 3 mice receiving gold beads coated with the NP DNA vector and the Quil A adjuvant; (Group 5) 3 mice receiving gold beads coated with the NP DNA vector coadministered immediately after an intradermal injection of Quil A; and (Group 6) 3 mice receiving gold beads coated with the NP DNA vector coadministered immediately after a subcutaneous injection of a solution containing Quil A.

The NP DNA vector contained a sequence encoding the influenza NP antigen (from the PR8 strain) and is described in Pertmer et al. (1995) Vaccine 13:1427–1430. All gold beads were loaded as described above at a bead loading rate of 0.5 mg Au/target and a DNA loading rate of 2.0 μg/mg Au. Administration with the PowderJect™ XR device was to two target sites at 400 psi operating pressure, and was a prime-only experiment. After one month, mice were sacrificed and blood and spleen samples collected for analysis as also described above. For the ELISPOT assay, the peptide used to stimulate the CTL precursors was TYQRTRALV (at 10–8M) (SEQ ID NO: 5) and the lysed influenza PR8 virus was used at 5 μg/mL for the Th stimulation. For chromium analysis, the peptide used to stimulate the responders was TYQRTRALV (at 10–5.5M) (SEQ ID NO: 5); and the peptide used to pulse the target was TYQRTRALV (at 10–5.5M) (SEQ ID NO: 5). For the ELISA, the capture antigen was PR8 NP antigen (Sprafas) at 1 mg/mL.

The results of the study are depicted below in Table 1. As can be seen, intracellular administration of Quil A in association with the DNA vector (Group 4) enhances antigen-specific T helper response, CTL and antibody responses, and is superior to extracellular intradermal (Group 5) or subcutaneous (Group 6) coadministration of the Quil A immediately prior to the DNA delivery for both induction of CTL and antibody responses.

TABLE 1

| Group # | Ave. CTLp SFC/10$^6$ cells | Ave. % Lysis (40:1 E/T) | Th1 Response (IFN-γ) | Th2 Response (IL-4) | IgG (Titer) |
|---|---|---|---|---|---|
| 1 | 0 | 0 | 0 | 0 | <100 |
| 2 | 18 | 12.6 | 15 | 3 | 14,642 |
| 3 | nd | 17.5 | nd | nd | 5,171 |
| 4 | 52 | 43.0 | 53 | 14 | 40,637 |
| 5 | 6 | 5.7 | 55 | 28 | 5,283 |
| 6 | 4 | 19.7 | nd | nd | 25,600 |

Example 3

Intracellular Coadministration of Quil A with DNA on Gold Beads to Enhance an Influenza NP-Specific Immune Response In order to help confirm the results seen above with Example 2, the following study was carried out. Experimental groups of Balb/c mice were set up as follows: (Group 1) 4 control mice receiving gold beads coated with irrelevant DNA via the PowderJect™ XR particle-mediated delivery device; (Group 2) 4 mice receiving gold beads coated with irrelevant DNA and Quil A coadministered via the PowderJect™ XR particle-mediated delivery device; (Group 3) 4 mice receiving gold beads coated with the NP DNA vector only via the PowderJect™ XR device; and (Group 4) 4 mice receiving gold beads coated with the NP DNA vector and the Quil A adjuvant.

Here again, the NP DNA vector contained a sequence encoding the influenza NP antigen (from the PR8 strain) and is described in Pertmer et al. (1995) Vaccine 13:1427–1430. All gold beads were loaded as described above at a bead loading rate of 0.5 mg Au/target and a DNA loading rate of 2.0 μg/mg Au. Administration with the PowderJect™ XR device was to two target sites at 400 psi operating pressure, and was a prime-only experiment. Vaccination was only given once, and after one month, mice were sacrificed and blood and spleen samples collected for analysis as also described above. For the ELISPOT assay, the peptide used to stimulate the CTL precursors was TYQRTRALV (at 10–8M) (SEQ ID NO: 5); and the lysed influenza PR8 virus was used at 5 μg/mL for the Th stimulation. For the chromium analysis, the peptide used to stimulate the responders was TYQRTRALV (at 10–8M) (SEQ ID NO: 5); and the peptide used to pulse the targets was TYQRTRALV (at 10–5.5M) (SEQ ID NO: 5). For the ELISA, the capture antigen was PR8 NP antigen (Sprafas) at 1 mg/mL.

The results of the study are depicted below in Table 2. As can be seen, intracellular administration of Quil A in association with the DNA vector (Group 4) provides for an enhanced antigen-specific T helper response, CTL response, and antibody response.

TABLE 2

| Group # | Ave. CTLp SFC/10$^6$ cells | Ave. % Lysis (50:1 E/T) | IgG (titer) |
|---|---|---|---|
| 1 | 6.5 | 0.3 | <100 |
| 2 | 0.5 | 0 | <100 |
| 3 | 14.5 | 17.0 | 16,846 |
| 4 | 25.0 | 28.8 | 62,706 |

Example 4

Intracellular Coadministration of Quil A with DNA on Gold Beads to Enhance an HIV gp120-Specific CTL Immune Response In order to determine whether coadministration of a composition containing a DNA vaccine vector that encodes the human immunodeficiency virus (HIV) gp120 antigen and Quil A adjuvant directly into cells can enhance an antigen-specific immune response, the following study was carried out. Experimental groups of Balb/c mice were set up as follows: (Group 1) 4 control mice receiving gold beads coated with irrelevant DNA via the PowderJect™ XR particle-mediated delivery device; (Group 2) 4 mice receiving gold beads coated with irrelevant DNA vector and Quil A and delivered via the PowderJect™ XR device; (Group 3) 3 mice receiving gold beads coated with the HIV gp120 DNA vector only delivered via the PowderJect™ XR device, primed once and boosted three times; (Group 4) 3 mice receiving gold beads coated with the HIV gp120 DNA vector only delivered via the PowderJect™ XR device, primed once and boosted once; (Group 5) 3 mice receiving gold beads coated with the HIV gp120 DNA vector and the Quil A adjuvant and coadministered via the PowderJect™ XR particle-mediated delivery device, primed once and boosted three times; and (Group 6) 3 mice receiving gold beads coated with the HIV gp120 DNA vector and the Quil A adjuvant and administered via the PowderJect™ XR particle-mediated delivery device, primed once and boosted once.

The HIV gp120 DNA vector contained a sequence encoding the HIV gp120 antigen (from the LAI strain) and is described in Heydenburg et al. (1994) AIDS Res. and Hum. Retroviruses 10:1433–1441. All gold beads were loaded as described above at a bead loading rate of 0.5 mg Au/target and a DNA loading rate of 2.0 μg/mg Au. Administration with the PowderJect™ XR device was to two target sites at 400 psi operating pressure. Varying numbers of vaccinations were carried out (some having one boost, others having three boosts), with vaccination administered every four weeks. Sacrifice of all mice was at week 14 of the study, and spleen samples were collected for analysis as described above. For the ELISPOT assay, the peptide used to stimulate the CTL precursors was RGPGRAFVTI (at 10–7M) (SEQ ID NO: 6). For the chromium analysis, the peptide used to stimulate the CTL responders and pulse the targets was RGPGRAFVTI (at 10–7M) (SEQ ID NO: 6).

The results of the study are reported below in Table 3. As can be seen, the results confirm the data seen above with the influenza antigen in that intracellular coadministration of Quil A and DNA vector enhanced the HIV gp120-specific CTL responses after a prime and one boost in vaccinated mice, with no significant difference when the mice were boosted three times.

TABLE 3

| Group # | Ave. % Lysis (50:1 E/T) |
|---|---|
| 1 | 3.2 |
| 2 | 3.5 |
| 3 | 36.7 |
| 4 | 14.7 |
| 5 | 32.7 |
| 6 | 35.4 |

Example 5

Intracellular Coadministration of Quil A with DNA on Gold Beads to Enhance an HBsAg-Specific CTL Immune Response In order to determine whether coadministration of a composition containing a DNA vaccine vector that encodes the hepatitis B virus surface antigen (HBsAg) and Quil A adjuvant directly into cells can enhance an antigen-specific immune response, the following study was carried out. Experimental groups of Balb/c mice were set up as follows: (Group 1) 4 control mice receiving gold beads coated with irrelevant DNA via the PowderJect™ XR particle-mediated delivery device; (Group 2) 4 mice receiving gold beads coated with the HBsAg DNA vector and administered via the PowderJect™ XR particle-mediated delivery device; and (Group 3) 4 mice receiving gold beads coated with the HBsAg DNA vector and the Quil A adjuvant and administered via the PowderJect™ XR particle-mediated delivery device. The experiment was repeated with the exact same experimental groups being used.

The HbsAg DNA vector contained a sequence encoding the HBV surface antigen is termed pWRG7128. The plasmid pWRG7128 contains, in addition to suitable control elements, a sequence encoding the hepatitis B surface antigen (HbsSAg) which is under the transcriptional control of a cytomegalovirus (CMV) promoter, and has been shown to produce HbsAg particles upon transfection into most cell types. The pWRG7128 plasmid was constructed as follows. A cloning vector pWRG7077 (Schmaljohn et al. (1997) J. Virol. 71: 9563–9569) was prepared to accept a HbsAg coding sequence by digesting the vector to completion with BamH1, followed by a partial digest with Hind3. After blunting the 5' overhangs by treatment with Klenow fragment and deoxyribonucleotides, the 4.3 kB vector fragment was isolated. The 1.35 kB HbsAg insert fragment (containing the untranslated pre-S2 sequence, the 226 amino acid HbsAg coding sequence of the adw strain, and the HBV enhancer element) was excised from plasmid pAM6 (ATCC, Rockford, Md.) by digesting with BamH1. After bluntending by treatment with the Klenow fragment and deoxyribonucleotides, the fragment was isolated and ligated into the 4.3 kB vector fragment described above. The resulting recombinants were screened for proper orientation of the insert and a correct isolate was identified and designated as an intermediate plasmid (pWRG7074). In order to remove the start of the codon of the X protein (present at the 3' end of the pAM6 1.35 kB insert), a 4.86 kB vector fragment was isolated from the pWRG7074 plasmid by digesting with Bgl2, blunt-ending with the Klenow fragment and deoxyribonucleotides, and then digesting with BstX1. Next, a 754 bp insert fragment was isolated from the pWRG7074 construct by digestion with Nco1, treating with mung bean nuclease, and digesting with BstX1. The resulting vector and insert fragments were then ligated together to form the clinical plasmid pWRG7128. All gold beads were loaded as described above at a bead loading rate of 0.5 mg Au/target and a DNA loading rate of 2.0 µg/mg Au. Administration with the PowderJect™ XR device was to two target sites at 400 psi operating pressure. Vaccination was only given once, and after one month, mice were sacrificed and spleen samples collected for chromium release (specific lysis) analysis as described above. For the ELISPOT assay, the peptide used to stimulate the CTL precursors was IPQSLD-SWWTSL (at 10–6M) (SEQ ID NO: 7). For the chromium analysis, a P815 cell line expressing the HBV surface antigen was used instead of peptide for stimulation of responders (at 40,000/well) and for effectors (at 30,000/well).

The results of the study are reported below in Table 4. As can be seen, the results confirm the data seen above with both the influenza antigen and the HIV antigen in that intracellular coadministration of Quil A and DNA vector enhanced the HBsAg-specific CTL responses.

TABLE 4

| % Specific Lysis at Effector: Target ratio | Group 2 animals, first experiment | Group 3 animals, first experiment | Group 2 animals, second experiment | Group 3 animals, second experiment |
|---|---|---|---|---|
| 17:1 | 26.9 | 44.2 | 53.4 | 78.6 |
| 5.6:1 | 16.5 | 36.3 | 34.7 | 70.9 |
| 1.9:1 | 7.4 | 18.0 | 22.3 | 41.9 |

Accordingly, novel vaccine compositions and methods of inducing an immune response are disclosed. Although preferred embodiments of the subject invention have been described in some detail, it is understood that obvious variations can be made without departing from the spirit and the scope of the invention as defined by the appended claims.

We claim:

1. Coated particles suitable for use in particle-mediated nucleic acid immunisation, which particles comprise core carrier particles coated with (1) a nucleic acid molecule comprising a sequence encoding an antigen; and (2) an adjuvant which is effective to enhance at least one component of an immune response elicited against the antigen, wherein the adjuvant is present in a form other than DNA.

2. The coated particles of claim 1, wherein the nucleic acid molecule is present in a vector construct.

3. The coated particles of claim 2, wherein the antigen is an antigen of a viral, bacterial, parasite or fungal pathogen.

4. The coated particles of claim 3, wherein the virus is selected from the group consisting of a hepatitis B virus (HBV), human immunodeficiency virus (HIV) and an influenza virus.

5. The coated particles of claim 3, wherein the antigen is a circumsporozoite (CS) antigen from a malarial parasite.

6. The coated particles of claim 1, wherein the antigen is a tumor-specific antigen or an antigen associated with an autoimmune disease.

7. The coated particles of claim 1, wherein the adjuvant is present in the form of a lipid.

8. The coated particles of claim 1, wherein the adjuvant comprises monophosphoryl lipid A.

9. The coated particles of claim 1, wherein the adjuvant is at least partially soluble in ethanol.

10. The coated particles of claim 1, wherein the adjuvant is an immune shift adjuvant which is effective to enhance the T helper 1 (Th 1) component of an immune response elicited against the antigen in an individual receiving said particles.

11. The coated particles of claim 1, wherein said core carrier particles are tungsten or gold particles.

12. The coated particles of claim 11, wherein the gold particles have a nominal size of from about 0.1 to about 10 μm.

13. A pharmaceutical composition comprising the coated particles of claim 1.

14. A method for eliciting an immune response against a selected antigen in an individual, said method comprising co-administering to the individual (1) a nucleic acid molecule comprising a sequence encoding an antigen; and (2) an adjuvant which is effective to enhance at least one component of an immune response elicited against the antigen, wherein the adjuvant is present in a form other than DNA, wherein the adjuvant is delivered directly into cells present at a target site in the individual in an amount sufficient to bring about said immune response and wherein the nucleic acid molecule and the adjuvant are coated onto core carrier particles.

15. The method of claim 14, wherein the nucleic acid and adjuvant are administered in (a) a single composition; or (b) separate compositions.

16. The method of claim 14, wherein the adjuvant is delivered prior to, subsequent to, or concurrently with, the nucleic acid.

17. The method of claim 14 wherein the nucleic acid molecule and/or the adjuvant is/are delivered using a particle-mediated delivery technique.

18. The method of claim 14, wherein the nucleic acid molecule is present in a vector construct.

19. The method of claim 14, wherein the antigen is an antigen of a viral, bacterial, parasite or fungal pathogen.

20. The method of claim 19, wherein the virus is selected from the group consisting of a hepatitis B virus (HBV), human immunodeficiency virus (HIV) and an influenza virus.

21. The method of claim 19, wherein the antigen is a circumsporozoite (CS) antigen from a malarial parasite.

22. The method of claim 14, wherein the antigen is a tumor-specific antigen or an antigen associated with an autoimmune disease.

23. The method of claim 14, wherein the adjuvant is present in the form of a lipid.

24. The method of claim 14, wherein the adjuvant comprises monophosphoryl lipid A.

25. The method of claim 14, wherein the adjuvant is at least partially soluble in ethanol.

26. The method of claim 14, wherein the adjuvant is an immune shift adjuvant which is effective to enhance the T helper 1 (Th 1) component of an immune response elicited against the antigen in an individual receiving said antigen.

27. The method of claim 14, wherein said core carrier particles are tungsten or gold particles.

28. The method of claim 27, wherein the gold particles have a nominal size of from about 0.1 to about 10 μm.

29. The method of claim 14 wherein the target site is epidermal tissue.

* * * * *